(12) United States Patent
Hazan et al.

(10) Patent No.: US 11,007,354 B2
(45) Date of Patent: May 18, 2021

(54) METHOD AND DEVICE FOR TREATMENT OF STRESS URINARY INCONTINENCE (SUI)

(71) Applicant: Continale Medical Pte. Ltd., Singapore (SG)

(72) Inventors: Yosef Hazan, Haifa (IL); Avshalom Shenhav, Haifa (IL)

(73) Assignee: Continale Medical Pte. Ltd., Singapore (SG)

( * ) Notice: Subject to any disclaimer, the term of this patent is extended or adjusted under 35 U.S.C. 154(b) by 267 days.

(21) Appl. No.: 15/746,446

(22) PCT Filed: Jul. 28, 2016

(86) PCT No.: PCT/IL2016/050832
§ 371 (c)(1),
(2) Date: Jan. 22, 2018

(87) PCT Pub. No.: WO2017/017688
PCT Pub. Date: Feb. 2, 2017

(65) Prior Publication Data
US 2018/0221634 A1      Aug. 9, 2018

Related U.S. Application Data

(60) Provisional application No. 62/198,155, filed on Jul. 29, 2015.

(51) Int. Cl.
*A61M 31/00*      (2006.01)
*A61M 25/00*      (2006.01)
*A61F 2/00*        (2006.01)

(52) U.S. Cl.
CPC ........... *A61M 31/00* (2013.01); *A61F 2/0022* (2013.01); *A61M 25/00* (2013.01);
(Continued)

(58) Field of Classification Search
CPC .......... A61M 31/00; A61M 2210/1085; A61M 2210/1089; A61M 2210/1092;
(Continued)

(56) References Cited

U.S. PATENT DOCUMENTS 4,043,345 A    8/1977   Kramann et al.
4,063,548 A    12/1977  Klatt et al.
(Continued)

FOREIGN PATENT DOCUMENTS

CN    1359307 A    7/2002
CN    1549733 A    11/2004
(Continued)

OTHER PUBLICATIONS

Frothingham, Scott. "What's the Average Hand Size for Men, Women, and Children?" Healthline, Aug. 7, 2019, www.healthline.com/health/average-hand-size. (Year: 2019).*
(Continued)

*Primary Examiner* — Bhisma Mehta
*Assistant Examiner* — James D Ponton
(74) *Attorney, Agent, or Firm* — JCIP; Joseph G. Chu; Jeremy I. Maynard

(57) ABSTRACT

A device for insertion of material into a urethra comprising: a nozzle with a rounded nozzle tip, sized for at least partial insertion into the urethra; and a source of compressed material coupled to the nozzle where a pressure of the compressed material is less than 200 cm $H_2O$; a control, for control of flow of material from the source through the nozzle; wherein a maximum extent of the device is less than 30 cm.

39 Claims, 22 Drawing Sheets

(52) U.S. Cl.
CPC .............. *A61M 2205/3331* (2013.01); *A61M 2205/581* (2013.01); *A61M 2205/583* (2013.01); *A61M 2205/587* (2013.01); *A61M 2210/1085* (2013.01); *A61M 2210/1089* (2013.01); *A61M 2210/1092* (2013.01); *A61M 2210/1096* (2013.01)

(58) Field of Classification Search
CPC .......... A61M 2210/1096; A61M 25/00; A61M 13/003; A61M 13/00; A61F 2/0022; A61B 5/20; A61B 5/202; A61B 5/204; A61B 5/205; A61B 2017/00805
See application file for complete search history.

(56) References Cited

U.S. PATENT DOCUMENTS

| | | | |
|---|---|---|---|
| 4,109,659 A * | 8/1978 | Sheridan | A61M 25/0119 604/271 |
| 4,612,939 A | 9/1986 | Robertson | |
| 5,019,032 A | 5/1991 | Robertson | |
| 5,090,424 A | 2/1992 | Simon et al. | |
| 6,021,781 A | 2/2000 | Thompson et al. | |
| 6,083,933 A * | 7/2000 | Hahn | A61K 31/737 424/9.2 |
| 6,119,697 A | 9/2000 | Engel et al. | |
| 6,447,462 B1 | 9/2002 | Wallace et al. | |
| 6,527,702 B2 | 3/2003 | Whalen et al. | |
| 6,544,240 B1 * | 4/2003 | Borodulin | A61F 2/0009 604/329 |
| 6,699,175 B2 | 3/2004 | Miller | |
| 7,112,177 B2 | 9/2006 | Christensen et al. | |
| 7,615,046 B2 | 11/2009 | Shehata | |
| 8,439,867 B2 | 5/2013 | Staskin | |
| 2001/0020162 A1 | 9/2001 | Mosel et al. | |
| 2002/0026209 A1 | 2/2002 | Hung | |
| 2002/0115906 A1 * | 8/2002 | Miller | A61M 13/003 600/31 |
| 2003/0023135 A1 * | 1/2003 | Ulmsten | A61B 1/32 600/29 |
| 2003/0036804 A1 | 2/2003 | Li et al. | |
| 2003/0229263 A1 * | 12/2003 | Connors | A61B 5/205 600/29 |
| 2004/0116903 A1 * | 6/2004 | Osman | A61M 3/0262 604/543 |
| 2004/0133068 A1 | 7/2004 | Miller | |
| 2005/0288639 A1 | 12/2005 | Hibner | |
| 2006/0100478 A1 | 5/2006 | Connors et al. | |
| 2008/0004566 A1 | 1/2008 | Sloan | |
| 2009/0171317 A1 * | 7/2009 | Versi | A61M 25/0017 604/517 |
| 2009/0312696 A1 | 12/2009 | Copa et al. | |
| 2010/0222802 A1 * | 9/2010 | Gillespie, Jr. | A61B 90/02 606/192 |
| 2012/0283701 A1 | 11/2012 | Shelso et al. | |
| 2013/0228178 A1 | 9/2013 | Rogers, Jr. | |
| 2015/0133779 A1 | 5/2015 | Yurek et al. | |

FOREIGN PATENT DOCUMENTS

| | | |
|---|---|---|
| CN | 102525687 A | 7/2012 |
| CN | 103327881 A | 9/2013 |
| CN | 103796613 A | 5/2014 |
| CN | 103796614 A | 5/2014 |
| CN | 203763642 U | 8/2014 |
| EP | 0258690 | 3/1988 |
| JP | S53-012198 | 8/1978 |
| JP | 2003-534884 | 12/2001 |
| JP | 2004-531341 A | 1/2003 |
| JP | 2003-534883 A | 11/2003 |
| JP | 2008-516674 | 4/2006 |
| JP | 2006-516001 A | 6/2006 |
| JP | 2011-513030 | 4/2011 |
| WO | WO 00/54701 | 9/2000 |
| WO | 0178576 A2 | 10/2001 |
| WO | WO 03/001994 | 1/2003 |
| WO | WO 2007/079152 | 7/2007 |
| WO | 2010068467 A | 6/2010 |
| WO | 2011081789 A1 | 7/2011 |
| WO | WO 2013/109163 | 7/2013 |
| WO | WO 2017/017688 | 2/2017 |

OTHER PUBLICATIONS

International Preliminary Report on Patentability dated Aug. 23, 2017 From the International Preliminary Examining Authority Re. Application No. PCT/IL2016/050832. (24 Pages).
International Search Report and the Written Opinion dated Jan. 12, 2017 From the International Searching Authority Re. Application No. PCT/IL2016/050832. (17 Pages).
Supplementary European Search Report and the European Search Opinion dated Mar. 4, 2019 From the European Patent Office Re. Application No. 16829967.5. (10 Pages).
First office action of Chinese Patent App. No. 201680043638.0 and English Translation thereof.
Third Office Action for Chinese Application No. 201680043638.0, dated Jan. 22, 2021.
Notification of Reasons for Refusal from Japan Patent Office for Japanese Patent Application No. 2017-565218 and English Translation thereof.
Second Office Action for Chinese Application No. 201680043638.0.

* cited by examiner

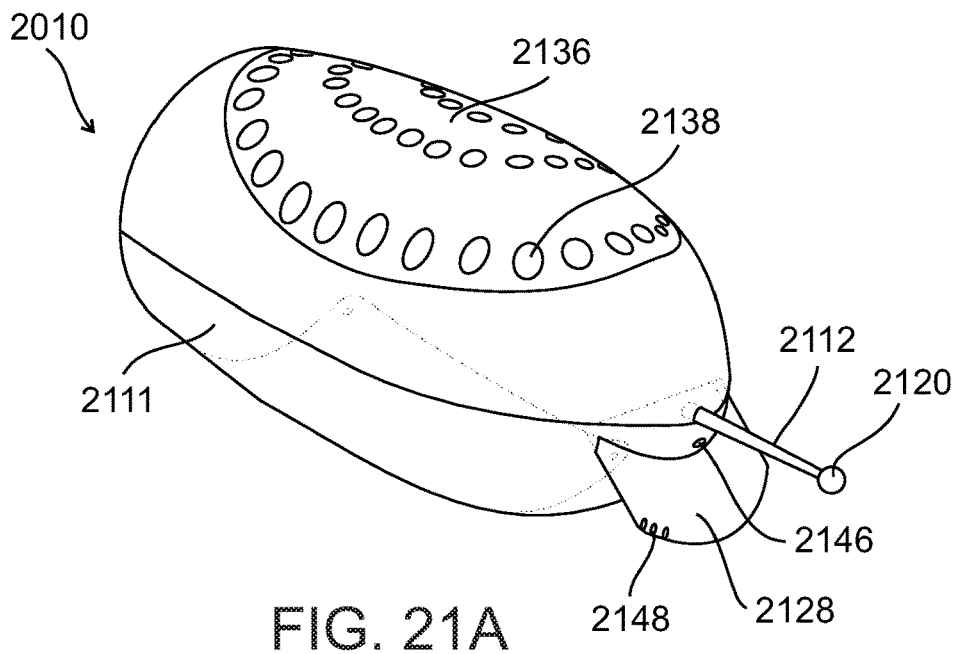
FIG. 21A
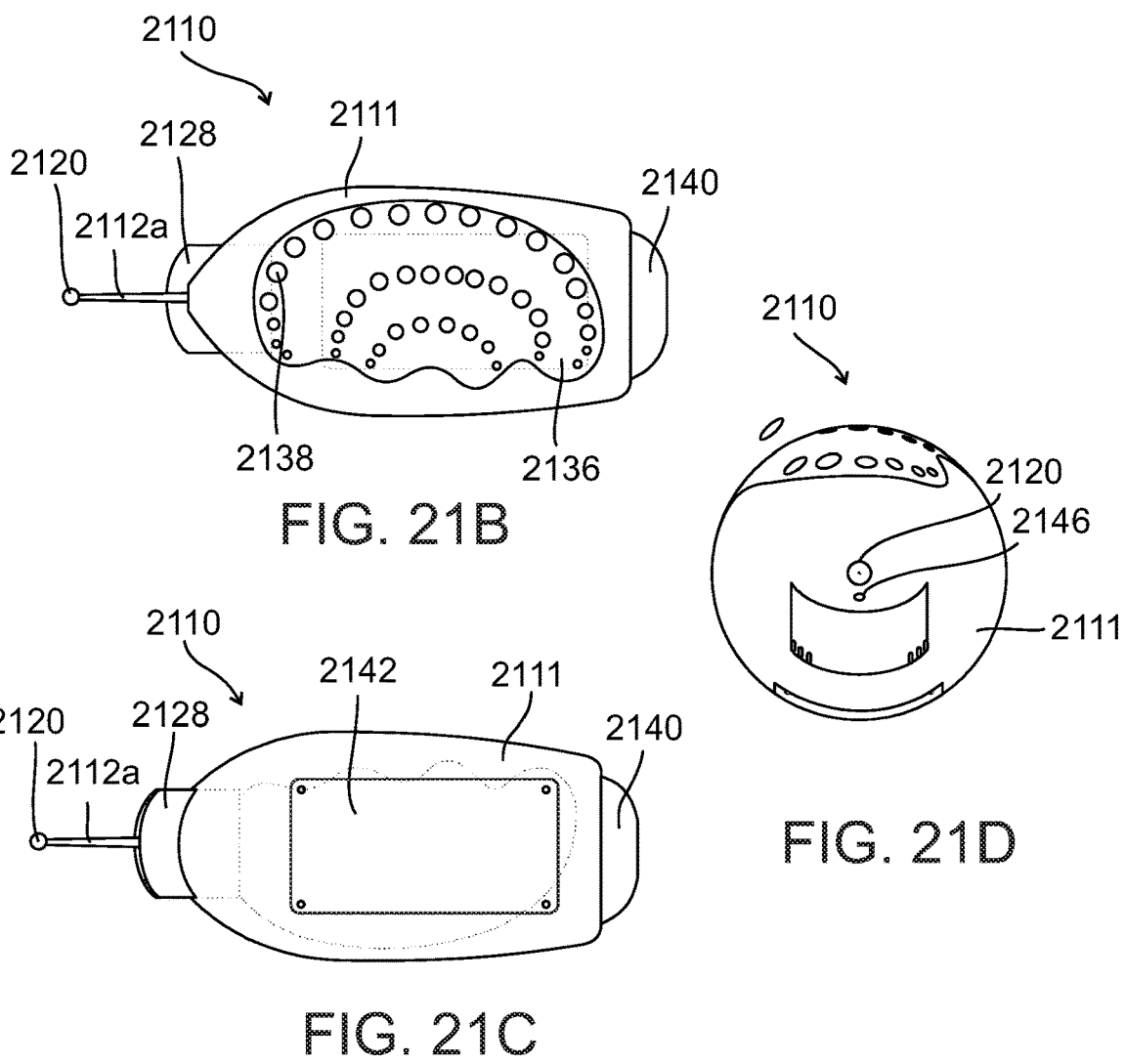
FIG. 21B
FIG. 21D
FIG. 21C

METHOD AND DEVICE FOR TREATMENT OF STRESS URINARY INCONTINENCE (SUI)

RELATED APPLICATIONS

This application is a National Phase of PCT Patent Application No. PCT/IL2016/050832 having International filing date of Jul. 28, 2016, which claims the benefit of priority under 35 USC § 119(e) of U.S. Provisional Patent Application No. 62/198,155 filed on Jul. 29, 2015. The contents of the above applications are all incorporated by reference as if fully set forth herein in their entirety.

FIELD AND BACKGROUND OF THE INVENTION

The present invention, in some embodiments thereof, relates to a method and device for treatment of incontinence and, more particularly, but not exclusively, to a method and device for treatment of stress urinary incontinence.

Stress urinary incontinence (SUI), is generally thought to be due to pelvic floor muscles which are not strong enough to prevent the passage of urine, especially during activities that increase intra-abdominal pressure, such as coughing, sneezing, or bearing down.

SUI can affect both males and females, but is more prevalent in females. Factors related to the strength of the pelvic floor are thought to contribute to SUI, such as; thinning and drying of the skin in the vagina or urethra (e.g. after menopause), weakened and stretched pelvic muscles (e.g. after childbirth). It is also thought that obesity, which can increase pressure on the bladder and muscles that control the bladder, urinary tract infections, vascular disease and operative complications can also be contributing factors to SUI.

A range of treatments for SUI exist. Treatments include non-surgical and surgical options. Non-surgical treatments include, for example; exercises to strengthen the pelvic floor (e.g. Kegel exercises), insertion of a pessary into the vagina which presses against the wall of the vagina and the nearby urethra, collagen and carbon injection near the urinary sphincter. Surgical treatments include, for example, sling and suspension procedures.

Additional background art includes International Patent Application No. WO 2000054701, U.S. Pat. No. 8,439,867, U.S. Patent Application No. US2005288639, U.S. Pat. Nos. 5,090,424, 4,612,939, 7,615,046, 6,527,702, 6,119,697, International Patent Application Publication No. WO13109163, U.S. Pat. No. 5,019,032, European Patent No. EP0258690, U.S. Pat. Nos. 6,699,175, 4,063,548, 7,112, 177, 6,447,462, 6,021,781.

SUMMARY OF THE INVENTION

According to an aspect of some embodiments of the present invention there is provided a device for insertion of material into a urethra comprising: a nozzle with a rounded nozzle tip, sized for at least partial insertion into the urethra; and a source of compressed material coupled to the nozzle where a pressure of the compressed material is less than 200 cm $H_2O$; a control, for control of flow of material from the source through the nozzle; wherein a maximum extent of the device is less than 30 cm.

According to some embodiments of the invention, at least a portion of the nozzle is sized and shaped to seal against the urethra. According to some embodiments of the invention, the nozzle is coupled to a device body; wherein the nozzle is sufficiently rigid such that the nozzle can be inserted into the urethra when the device is directed using the device body. According to some embodiments of the invention, the pressure of the compressed material opens the urethra from a nozzle tip to the bladder. According to some embodiments of the invention, the nozzle comprises a portion normally inverted inside body of the nozzle; wherein the pressure of the material uninverts the portion.

According to an aspect of some embodiments of the present invention there is provided a device for insertion of material into a urethra comprising: a source of compressed material where a pressure of the compressed material is less than 200 cm $H_2O$; a rounded nozzle, coupled to the source, adapted to form a seal against genital tissue around the urethra, the seal able to withstand the pressure of the compressed material; a control, for control of flow of material from the source through the nozzle; wherein the pressure is sufficient to open the urethra from a urethral opening to a bladder; wherein a maximum extent of the device is less than 30 cm.

According to some embodiments of the invention, the source comprises a pressurized material container. According to some embodiments of the invention, the source comprises: a material container; an inlet for collection of compressible material; and a pump coupled to the inlet, for compression of collected material into the material container.

According to some embodiments of the invention, the control prevents more than a maximum quantity of material from being dispensed within a time period.

According to some embodiments of the invention, the device comprises a positioning element for aligning the nozzle to the urethra. According to some embodiments of the invention, at least a portion of the positioning element is sized and shaped for placement in a body portion. According to some embodiments of the invention, the positioning element comprises a visual element to provide a user with at least one visual clue as to a location of at least a portion of the device with respect to a urethra. According to some embodiments of the invention, the positioning element comprises a mirror. According to some embodiments of the invention, the positioning element comprises a camera.

According to some embodiments of the invention, the compressed material is a gas. According to some embodiments of the invention, the compressed material is atmospheric air. According to some embodiments of the invention, the compressed material is a mixture of liquid and compressible elements. According to some embodiments of the invention, the compressible elements are gas bubbles. According to some embodiments of the invention, the material comprises medication. According to some embodiments of the invention, the medication is selected from the group consisting of chemotherapy medication, antibiotics, bladder over activity mediation and combinations thereof.

According to an aspect of some embodiments of the present invention there is provided a non-traumatic method of treatment of stress urinary incontinence comprising: introducing into a urethra less than 200 cc of pressurized material, where a pressure of the material is less than 200 cm $H_2O$ and the pressure is sufficient to open at least a portion of the urethra proximal to a bladder, whereby the material travels into a bladder.

According to some embodiments of the invention, the introducing is repeated.

According to some embodiments of the invention, less than a maximum quantity of material, is dispensed in a time period.

According to some embodiments of the invention, the introducing is upon a user input. According to some embodiments of the invention, the quantity of material is defined by the user input.

According to some embodiments of the invention, the method comprises providing compressed material. According to some embodiments of the invention, providing comprises compressing air.

According to some embodiments of the invention, the material in the bladder reduces a peak bladder shock pressure response to below a pressure at which the urethra opens ($p_{ura}$).

According to some embodiments of the invention, the method comprises aligning a nozzle to a user urethra.

According to some embodiments of the invention, the introducing is by a user; and wherein the urethra is a user urethra.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 21A is a simplified schematic of a side view of a device, according to some embodiments of the invention;

FIG. 21B is a simplified schematic of a top view of a device, according to some embodiments of the invention;

FIG. 21C is a simplified schematic of a bottom view of a device, according to some embodiments of the invention;

FIG. 21D is a simplified schematic of a front view of a device, according to some embodiments of the invention;

DESCRIPTION OF SPECIFIC EMBODIMENTS OF THE INVENTION

Figure 1:
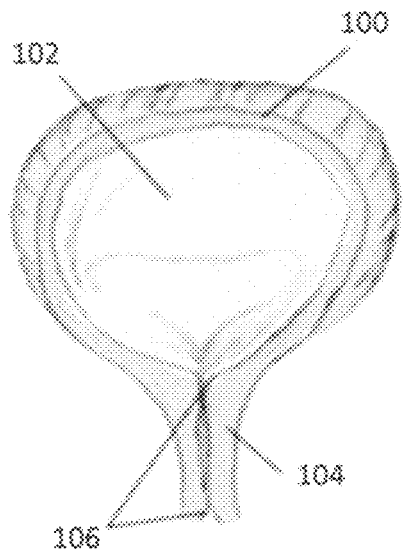
FIG. 1 is a simplified schematic cross sectional view of a bladder.

The present invention, in some embodiments thereof, relates to a method and device for treatment of incontinence and, more particularly, but not exclusively, to a method and device for treatment of stress urinary incontinence.

Overview

A broad aspect of some embodiments of the invention relates to changing mechanical properties of the bladder, such that a pressure response of the bladder to an inter-abdominal pressure wave (e.g. due to coughing, sneezing, laughing, lifting a heavy object, exercise etc.) is damped and/or spread. In some embodiments, an internal peak bladder pressure is reduced and/or delayed (e.g. internal peak bladder pressure is reduced below a pressure at which the urethra opens, sometimes termed urethra pressure ($p_{ura}$)).

In some embodiments, delay of the peak bladder pressure increases effectiveness of one or more mechanical mechanism of the urinary system in resisting urine leakage e.g. a kinking of the urethra.

In some embodiments, the bladder contains a material with higher compressibility than urine, herein termed 'cushion material'. Optionally, cushion material is unrestrained within the bladder.

An aspect of some embodiments of the invention relates to introducing one or more material into the bladder through the urethra, which material is herein termed 'introduced material'. In some embodiments, the material is introduced under pressure through the urethra. In some embodiments, introduced material is a fluid.

In some embodiments, introducing material does not damage user tissue, for example, in some embodiments, a quantity and/or pressure of material is less than a quantity and/or pressure of material that causes damage to the urethra and/or bladder. For example, a quantity of introduced material is less than an amount of material which abnormally distends and/or ruptures the bladder. For example, a pressure of introduced material is less that a pressure at which the urethral tissue is abnormally distended and/or ruptured.

In some embodiments, introduced material is gas, for example, inert gas (e.g. argon). In some embodiments, the material is mixture of liquid and compressible elements (e.g. a particle suspension where the particles are compressible). In some embodiments, the material is a mixture of gas bubbles and liquid.

In some embodiments, introduced material has higher compressibility than urine.

In some embodiments, introduced material includes medication.

In some embodiments, introduced material results in a material of higher compressibility inside the bladder, for example, in some embodiments, the introduced material undergoes a chemical or physical change (e.g. chemical reaction with urine, dissolution of a gas dissolved in the introduced material) once inserted into the urethra (e.g. inside the bladder), resulting in cushion material within the bladder.

Optionally, in some embodiments, the material introduced into the bladder mixes with urine within the bladder, increasing the compressibility thereof.

In some embodiments, treatment is self-treatment or personal use where a user initiates introduction of material into the user's urethra.

In some embodiments, treatment is repeated, for example, more than one time a day, several times a day, every time the user urinates.

In some embodiments, a quantity of dispensed material for each treatment is uniform. In some embodiments, a quantity of dispensed material is personalized. In some embodiments, a user defines (e.g. through a user interface) a quantity of dispensed material, optionally for each treatment. In some embodiments, the device dispenses up to a maximum quantity of material during a time period, for example to prevent, over a number of treatments, introducing a damaging amount of material.

An aspect of some embodiments of the invention relates to a device for introducing a material into the urethra, whereby the material then travels into the bladder.

In an exemplary embodiment, the device includes a nozzle, through which material is introduced into the urethra. In some embodiments, at least a portion of the nozzle is inserted into the urethra. Optionally, a tip of the nozzle is rounded and/or soft such that insertion of the tip is non-damaging to genital tissue. For example, during insertion, and/or at pressures required to achieve insertion of the nozzle, the nozzle tip does not cut and/or bruise genital tissue.

In some embodiments, a rounded nozzle tip includes an edge with a radius of curvature of 0.01-3 mm, or 0.05-1 mm, or 0.1-1 mm, or more than 0.01 mm, or more than 0.1 mm, or more than 0.5 mm, or lower, or higher, or intermediate ranges or values.

In some embodiments, the device nozzle includes an inverted section disposed inside the nozzle. During dispensing of material, the section uninverts (e.g. due to pressure of material dispensing through it). A potential benefit being, for example, that contamination on the nozzle tip, for example, from the urethra (e.g. bacteria) is not introduced with material into the bladder and/or further into the urethra. In some embodiments, the inverted section uninverts by rolling. Optionally, during dispensing, the inverted section protrudes increasing an extent (e.g. length) of the nozzle.

In some embodiments, the device includes one or more portion and/or element for sealing the device against user tissue, for example, so that dispensed material from the device enters the urethra and/or so that material within the urethra does not escape the body. In some embodiments, a seal of a nozzle against user tissue is sufficient to withstand a pressure of introduced material.

In an exemplary embodiment, a portion of the device is not inserted into the urethra, for example, in some embodiments, a nozzle is placed over the urethral opening. In some embodiments, a nozzle placed over the urethral opening forms a seal against genital tissue around the urethra sufficient to withstand a pressure of introduced material. In some embodiments, the tip is rounded and/or soft such that, at a pressure sufficient to generate a seal with user tissue, the nozzle does not cut and/or damage user genital tissue.

Optionally, in some embodiments, the device stores material to be introduced under pressure, for example in a canister e.g. gas canister. Alternatively or additionally, in some embodiments, the device pressurizes the material to be introduced, for example, prior to introduction into the urethra, e.g. the device includes a pump for pressurizing the material.

In some embodiments, the device includes a user interface through which a user initiates dispensing of material.

Optionally, in some embodiments, the device includes one or more positioning element to assist in positioning the nozzle at the user urethra.

In some embodiments, a positioning element is a mechanical element, optionally attached to the device, which is placed on and/or into a body portion (e.g. in the vagina, in the anus, on the leg) the placement of which aligns the nozzle with the urethral opening and/or the urethra.

In some embodiments, a positioning element provides clues, for example, visual and/or audio cues, (e.g. to guide positioning of the device). In some embodiments, a visual element (e.g. mirror, camera), provides a user feedback as to treatment. For example, in some embodiments, a user inserts material until seeing a visual clue (e.g. escape of a quantity of material and/or urine from the urethra).

In some embodiments, a positioning element includes one or more sensor, for example, a position sensor providing measurements e.g. as to the position of the nozzle (e.g. with respect to a marker, with respect to a user urethra).

In some embodiments, one or more positioning element includes one or more visual element, for example, a mirror and/or camera to assist the user (e.g. during self-treatment) in positioning the device. In some embodiments, the visual element provides visual clues to the user as to a location of one or more portion of the device with respect to user anatomy, e.g. urethral opening.

In some embodiments, the device is of dimension and weight such that a user self-treating can hold and/or position the device, optionally with one hand.

In some embodiments, one or more portion of the device is personalized, for example, shaped to fit an individual anatomy. In some embodiments, a positioning element is personalized, for example, a portion of the device, when placed, for example, onto and/or into a part of the user's body, aligns the device with the urethral opening.

An aspect of some embodiments of the invention relates to a method and device for introduction of medication into the urethra and/or bladder.

In some embodiments, introduced material includes medication, for example chemotherapy medication e.g. for bladder cancer, for example antibiotic/s e.g. for recurrent urinary tract infections (UTI), for example medication for local treatment of bladder over activity.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Change in Mechanical Properties of the Bladder

Generally, stress urinary incontinence (SUI) is associated with reduced mechanical resistance of the urethra, held closed by the urethral sphincter. If the mechanical resistance of the urethra is lower than a pressure of urine against the closure, urine will leak through the urethra. Intra-abdominal pressure waves, "shocks", for example, those emanating from the diaphragm (e.g. upon coughing, sneezing, laughing) cause an increase in pressure inside the bladder as the wave passes. If a shock or abdominal pressure wave causes the pressure inside the bladder to rise above $p_{ura}$, then urine leaks through the urethra.

Mechanical properties of the urethra in an individual can fluctuate with time, for example, kinking of the urethra, where movement of internal organs (e.g. upon an intra-abdominal pressure wave) exert closing pressure on the urethra, may increase $p_{ura}$ temporarily. SUI is also associated with a change in position of the urethra within the abdominal cavity due to, for example, weakened pelvic floor muscles, resulting in reduced kinking of the urethra.

In some embodiments, a material introduced into the bladder 'dampens' or 'spreads' the bladder's internal pressure response to an intra abdominal pressure wave or shock.

Figure 2:
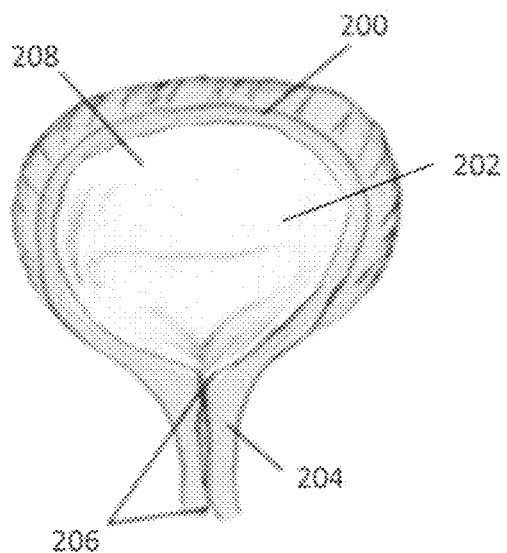
FIG. 2 is a simplified schematic cross sectional view of a bladder, according to some embodiments of the invention.

FIG. 1 is a simplified schematic cross sectional view of a bladder 100. Bladder 100 holds urine 102 and a urethra 104 is held closed by sphincter 106. FIG. 2 is a simplified schematic cross sectional view of a bladder 200, according to some embodiments of the invention. Bladder 200 includes fluid or material 208 of higher compressibility than urine 202.

Figure 3:
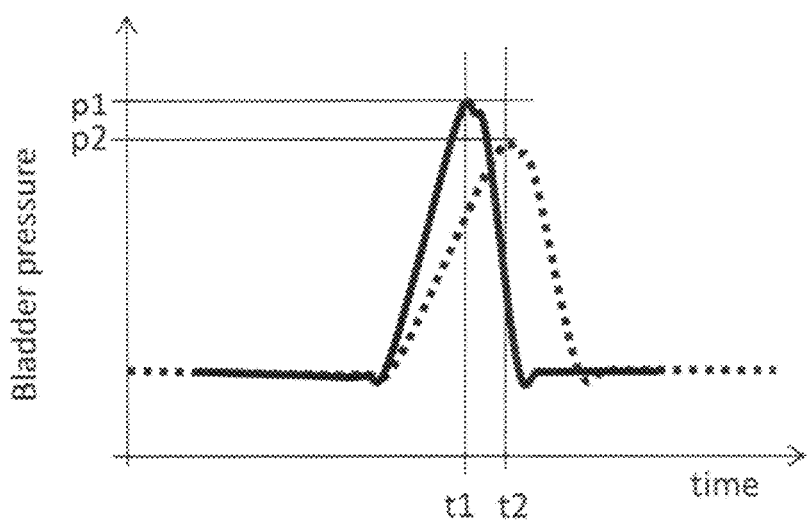
FIG. 3 is a is a simplified graphical representation of bladder pressure in response to an intra-abdominal pressure wave, with time, according to some embodiments of the invention.

FIG. 3 is a simplified graphical representation of bladder pressure in response to an intra abdominal pressure wave, with time, (a bladder shock pressure response) according to some embodiments of the invention. In FIG. 3, the solid line illustrates bladder pressure of the bladder illustrated in FIG. 1 and the dashed line illustrates bladder pressure for a bladder containing at least a portion of material of higher compressibility than urine, e.g. bladder 200 illustrated in FIG. 2.

In some embodiments, peak bladder pressure in the bladder, upon a shock, is reduced; p2 is lower than p1. In some embodiments, peak bladder pressure in the bladder, upon a shock, is delayed; t2 is later than t1. In some embodiments, 'spreading' or 'dampening' of bladder pressure response corresponds with reduction of peak bladder pressure and/or delay of peak bladder pressure.

Exemplary Method

Figure 4:
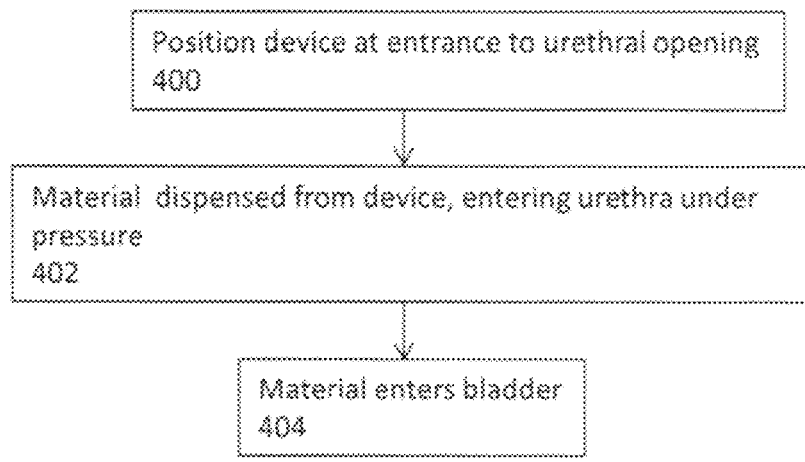
FIG. 4 is a flowchart of a method of treatment of stress urinary incontinence, according to some embodiments of the invention.

FIG. 4 is a flowchart of a method of treatment of stress urinary incontinence, according to some embodiments of the invention. FIG. 4 describes an exemplary method of placing material of higher compressibility than urine into a bladder, some aspects and potential benefits of which, for example, are described above.

At 400, the treatment begins by placing at least a portion of a device or into the urethral opening. At 402, material is dispensed from the device (e.g. after user activation of the device) into the urethra, under pressure. At 404, material that has been introduced to the urethra enters the bladder.

Exemplary Quantity of Material

In some embodiments, a treatment includes a single insertion of a dose of material into a urethra. In some embodiments, each treatment (e.g. over a time duration of less than 10 minutes) includes several discrete introductions of material. For example, in some embodiments, during a treatment, more than one dose of material is introduced into the urethra, optionally with a pause between doses (e.g. a pause of up to a second, 5 seconds, more than a minute. In some embodiments, during a treatment including multiple doses, the urethra closes in-between doses.

In some embodiments, in a treatment, 40 cc of material is introduced. In some embodiments, in a treatment 50 cc of material is introduced. In some embodiments, in a treatment, 20 cc-60 cc of material is introduced. In some embodiments, a quantity of material less than a quantity which causes trauma to the bladder is introduced, in a treatment (e.g. less than 500 cc, less than 400 cc, less than 200 cc, less than 100 cc, less than 50 cc).

In some embodiments, a volume of introduced material refers to a volume of the introduced material inside the bladder, where the material is under an internal bladder pressure. In some embodiments, a volume of introduced material refers to a volume of the introduced material under atmospheric pressure.

In some embodiments, a quantity of material to be introduced in a treatment is defined by measuring a user bladder capacity (e.g. the volume of urine contained by a bladder at which involuntary urination occurs) for example, introduced material quantity is less than 50%, less than 30%, less than 20%, less than 10%, of a bladder capacity.

In some embodiments, a user adjusts the quantity of introduced material, optionally each time the user uses the device, for example, in some embodiments, a user introduces material until the user feels the urge to urinate.

In some embodiments, for example, a user and/or medical professional/technician defines a quantity of material to be introduced (e.g. before each personal treatment, during a treatment, upon calibration of the device).

Exemplary Treatment

In some embodiments, treatment is repeated, for example, several times a day (e.g. each time a user urinates).

Optionally, the user urinates before treatment. Alternatively, in some embodiments, treatment is of a full bladder and the user optionally urinates after treatment.

In some embodiments, introduction of material displaces urine, for example, as material is introduced or after material is introduced, urine escapes the bladder through the urethra. In some embodiments, a bladder is substantially filled with material substantially emptying the bladder of urine. A potential benefit being the ability to empty the bladder, for example, as a treatment for users with difficulty in urination and/or difficulty in emptying the bladder sufficiently.

Some individuals e.g. men with enlarged prostates, are not able to fully empty their bladder by urinating. These individuals have a non-zero bladder volume after an attempt to fully empty the bladder through urination. The residual volume of urine remaining within the bladder is herein termed a bladder "dead volume".

In some embodiments, a bladder dead volume is 0.5-300 cc, or 1-100 cc, or 2-50 cc. In some embodiments, once introduced material is within the bladder, the user urinates, returning the bladder to the dead volume. Then, in some embodiments, at least a part of the residual dead volume is filled with cushion material (urine has been replaced by cushion material in the dead volume). A potential benefit being reduced negative effects of a dead volume (e.g. infection), a further potential benefit being, for example, as cushion material is compressible, the weight of the user's body may act to collapse the bladder to a lower (and/or substantially zero) dead volume.

Exemplary Pressure

In some embodiments, material is inserted at the entrance to the urethra. In some embodiments, pressurized insertion of material opens the urethra. In some embodiments, a pressure of insertion material is higher than $p_{ura}$, such that the material opens the urethra and/or travels through the urethra to the bladder. In some embodiments, the urethra is partially or fully opened mechanically, (e.g. by insertion of a stick, tube, catheter).

Generally, $p_{ura}$ for women with SUI is approximately 40:60 cm $H_2O$. In some embodiments, material is inserted into the urethra at a pressure of more than 40:60 cm $H_2O$. In some embodiments, material is inserted into the urethra at a pressure of 100 cm $H_2O$ or more. In some embodiments, the urethra is at least partially opened mechanically, and material is introduced into the urethra at a pressure of up to 70 cm $H_2O$.

In some embodiments, a pressure of said compressed material is less than a pressure which causes damage, for example, to the urethra and/or bladder. In some embodiments, the pressure of compressed material is less than 600 cm $H_2O$, or less than 300 cm $H_2O$, or less than 200 cm $H_2O$, or less than 100 cm $H_2O$.

Exemplary Material Type

In some embodiments, introduced material is a gas, for example, air. In some embodiments, introduced material is inert. In some embodiments, introduced material is an inert gas, for example, argon, nitrogen, helium. In some embodiments, material introduced is a liquid with dissolved gas, for example, carbonated water. In some embodiments, material introduced is a mixture of gas bubbles and liquid, for example a water and air bubble mixture, carbonated water.

In some embodiments, material introduced is a mixture of liquid and compressible elements, for example a suspension of liquid and encapsulated gas particles. In some embodiments, compressible elements are sufficiently small and/or the mixture is of sufficiently low viscosity such that the mixture flows through an opened urethra (e.g. a channel with a smallest cross-sectional dimension of 0.5 mm or less, of 1 mm or less, of 2 mm or less).

In some embodiments, introduced material includes medication, for example chemotherapy medication e.g. for bladder cancer, for example antibiotic/s e.g. for recurrent urinary tract infections (UTI), for example medication for local treatment of bladder over activity.

Exemplary Self-Treatment

In some embodiments, treatment is self-treatment or personal use where a user initiates introduction of material into the user's urethra.

In some embodiments, delivery of material to the urethra (e.g. self-treatment) is carried out when the user (or patient) is seated, for example on a toilet (e.g. so that any leakage of urine associated with introduction of material is easily disposed). In some embodiments, delivery of material to the urethra (e.g. self-treatment) is carried out when the user is lying down (e.g. on a bed), for example in a supine position. In some embodiments, delivery of material to the urethra (e.g. self-treatment) is carried out when the user is reclining, optionally with the knees spread and/or in a raised position.

In some embodiments, a user self-treating holds the device in one hand and holds user anatomy with the other hand. In some embodiments, positioning of the device is by moving the device and/or the user anatomy. For example, in some embodiments, a male user holds his penis in one hand and the device in the other hand and positioning of the device is by moving of the device and/or penis. For example, in some embodiments, a female user holds the device in one hand and holds, for example, the labia open with the other hand. Optionally, in some embodiments, once the device is positioned, the user holds the device in both hands. Alternatively, in some embodiments, a user self-treating holds the device in both hands during positioning and/or after positioning.

Exemplary Treatment of a Full Bladder

Figure 11:
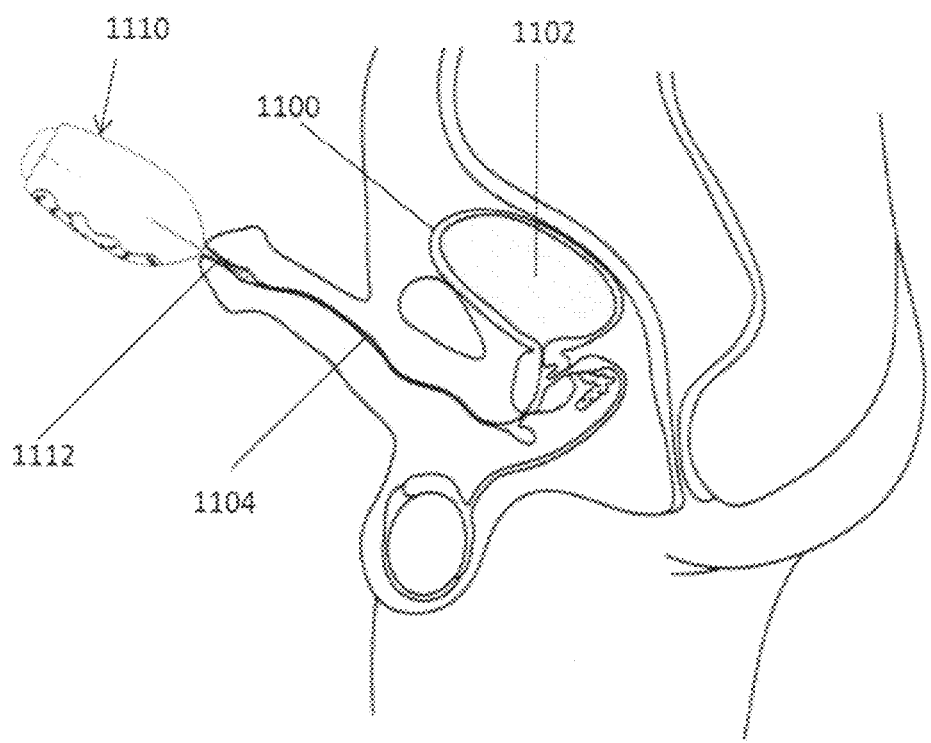
FIG. 11 is a simplified cross sectional view of a male with a full bladder and a simplified side view of a device, according to some embodiments of the invention.

In some embodiments, material is introduced to the urethra when the bladder is substantially full, for example, when a user feels the urge to urinate and/or when the bladder volume is more than 100 cc. FIG. 11 is a simplified cross sectional view of a male with a full bladder and a simplified side view of a device 1110, according to some embodiments of the invention. A portion of a nozzle 1112 is inserted into a urethra 1104 of the male.

Figure 12:
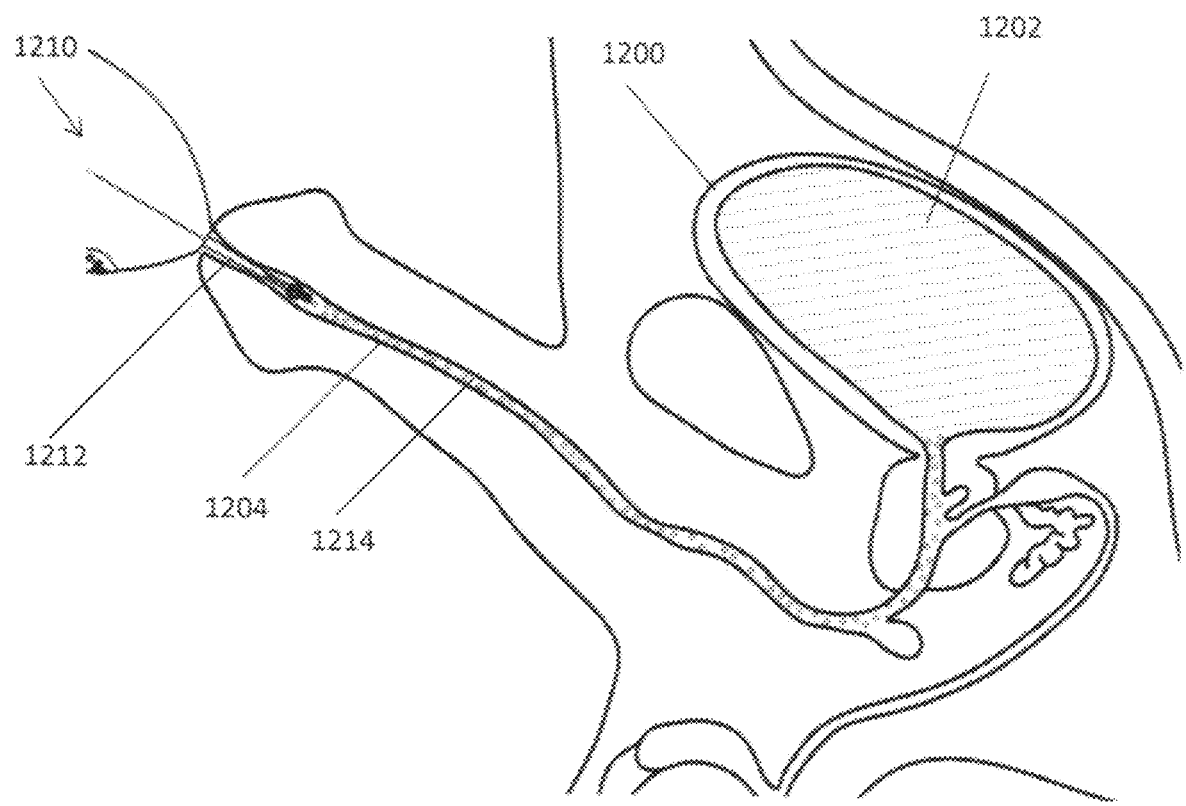
FIG. 12 is a simplified cross sectional view of a male with a full bladder (e.g. the user experiences the urge to urinate) undergoing treatment, according to some embodiments of the invention.

FIG. 12 is a simplified cross sectional view of a male with a full bladder undergoing treatment, according to some embodiments of the invention. A nozzle 1212 of a device 1210 is introducing pressurized material 1214 into a urethra 1204. Introduced material 1214 has opened urethra 1204 from between a bladder 1200 and nozzle 1212 and introduced material 1214 is entering bladder 1200. Bladder 1200 is full of urine 1202.

Figure 13A:
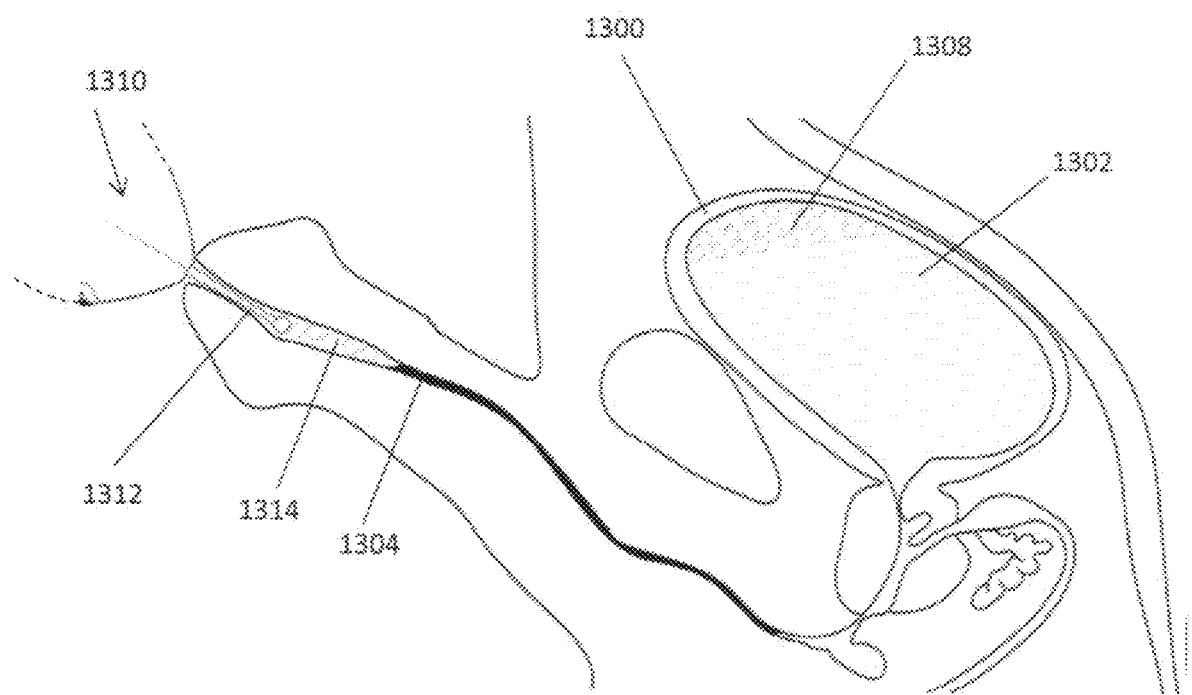
FIG. 13A illustrates a cross sectional view of a male with cushion material in a bladder and a side view of a portion of a device introducing additional material into a urethra, according to some embodiments of the invention.

In some embodiments, material is introduced into the urethra when cushion material is already in the bladder, herein termed 'additional material'. FIG. 13A illustrates a cross sectional view of a male with cushion material 1308 in a bladder 1300 and a side view of a portion of a device 1310 introducing additional material 1314 into a urethra 1304, according to some embodiments of the invention.

For example, in some embodiments, a user inserts additional material before previously inserted material forming cushion material has exited the user, for example, additional material is inserted a time duration after a previous insertion (e.g. a few minutes, several hours).

Exemplary Embodiment—Inserted Nozzle

Figure 5:
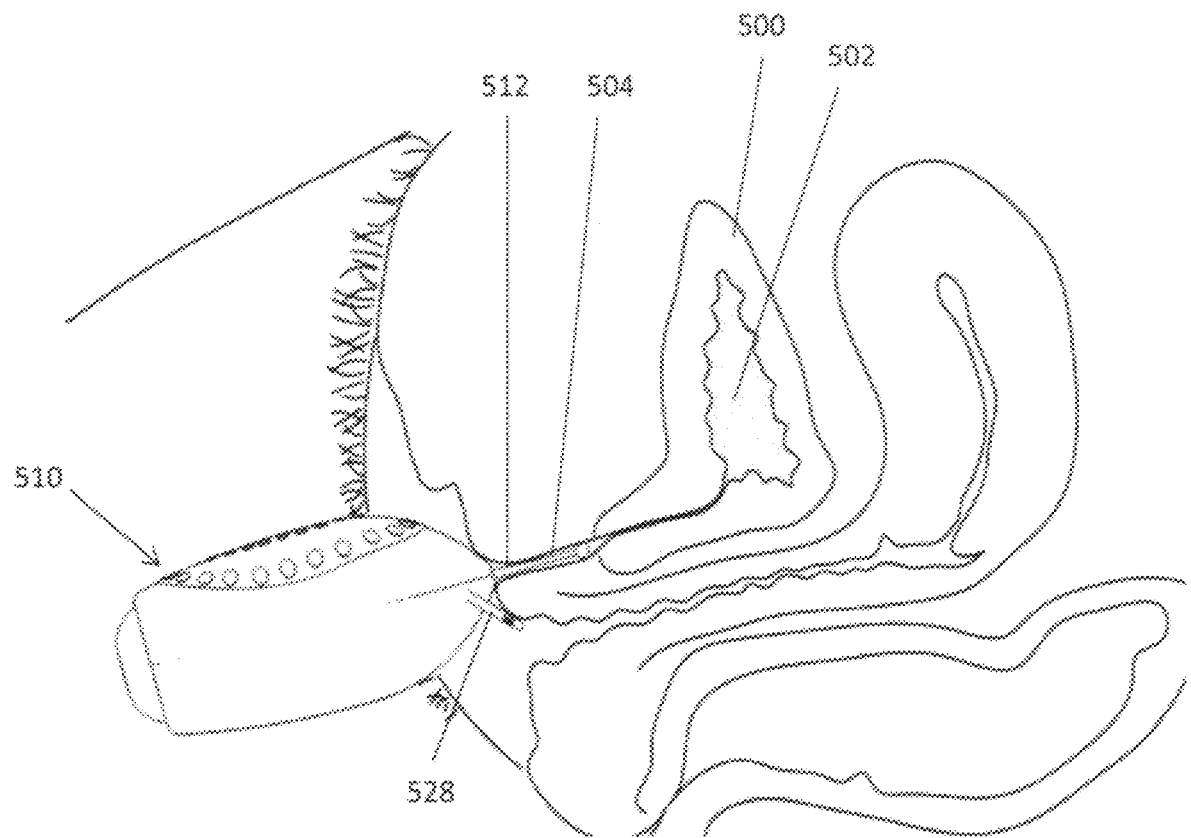
FIG. 5 is a simplified schematic side view of a device and a cross sectional view of a female, with a portion of the device inserted into a urethra of the female, according to some embodiments of the invention.

Optionally, in some embodiments, at least a portion of the device is inserted into a urethra, for example, thereby mechanically opening at least a section of the urethra. FIG. 5 is a simplified schematic side view of a device 510 and a cross sectional view of a female, with a portion of the device inserted into a urethra 504 of the female, according to some embodiments of the invention.

In some embodiments, the nozzle is lubricated (using e.g. water, K-Y Jelly®, Surgilube®) before use, for example, in some embodiments, to smooth insertion of the nozzle into the urethra, for example, in some embodiments, to assist in sealing the device against user tissue.

In some embodiments, device 510 includes a nozzle 512 at least part of which is inserted into urethra 504. In some embodiments, nozzle 512 is elongated. In some embodiments, nozzle 512 is inserted 20 mm-30 mm or 10 mm-50 mm or less than 20 mm or more than 50 mm into urethra 504. In some embodiments, nozzle is inserted through urethra 504 and reaches bladder 500.

In some embodiments, mechanical opening of the urethra by insertion of nozzle 512 reduces $p_{ura}$ (e.g. temporarily). In some embodiments, pressure of introduced material, for example when a nozzle is inserted into the urethra, is 70 cm $H_2O$ or more.

Figure 6A:
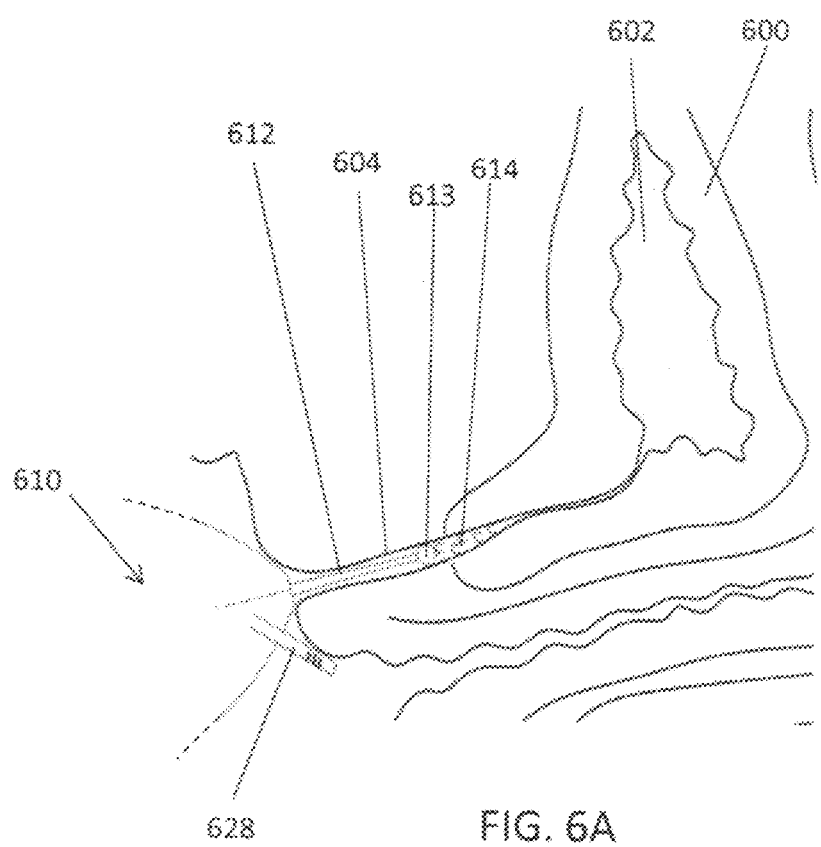
FIG. 6A is a cross sectional view of a female and simplified schematic side view of a portion of a device introducing material into a urethra of the female, according to some embodiments of the invention.

FIG. 6A is a cross sectional view of a female and simplified schematic side view of a portion of a device 610 introducing material 614 into a urethra 604 of the female, according to some embodiments of the invention. For clarity, introduced material 614 is illustrated as fluid including bubbles. In some embodiments, material 614 is introduced through the nozzle 612, when nozzle 612 is positioned inside urethra 604. In some embodiments, a pressure of introduced material opens the urethra, for example, in FIG. 6A, the urethra is partially opened by insertion of nozzle 612 and partially opened by pressure of introduced material 614.

Figure 6B:
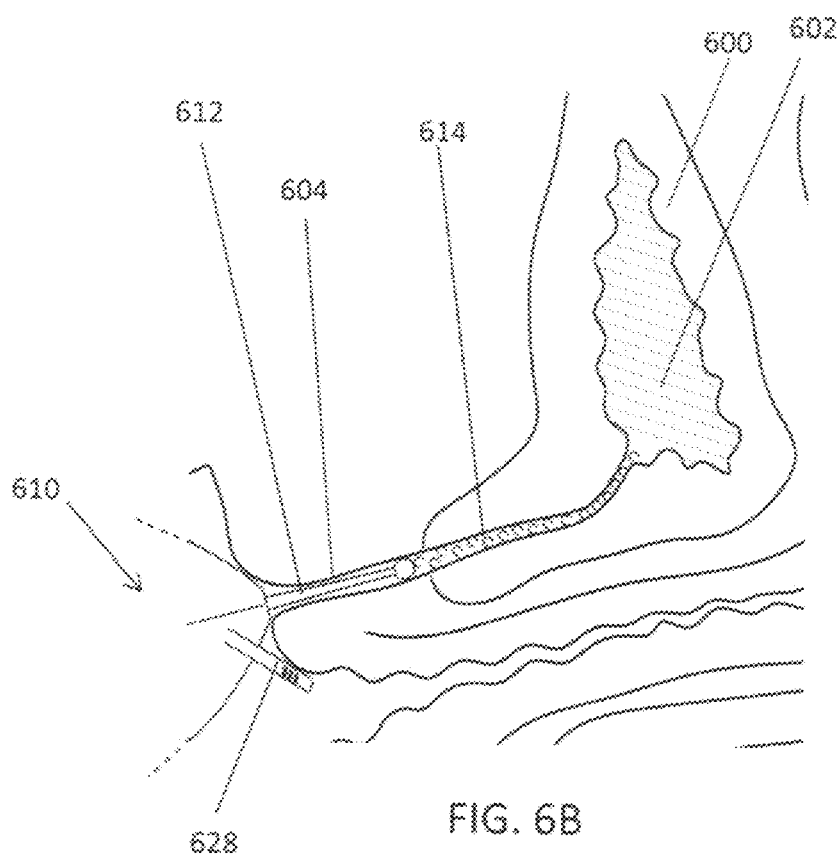
FIG. 6B is a cross sectional view of a female and simplified schematic side view of a portion of a device introducing material into a urethra of the female, according to some embodiments of the invention.

In some embodiments, at least a portion of material 614 introduced into urethra 604 travels along urethra 604, into bladder 602. FIG. 6B is a cross sectional view of a female and simplified schematic side view of a portion of a device 610 introducing material into a urethra 604 of the female, according to some embodiments of the invention. In FIG. 6B urethra 604 has been opened up to the bladder and introduced material 614 is entering the bladder.

Figure 7:
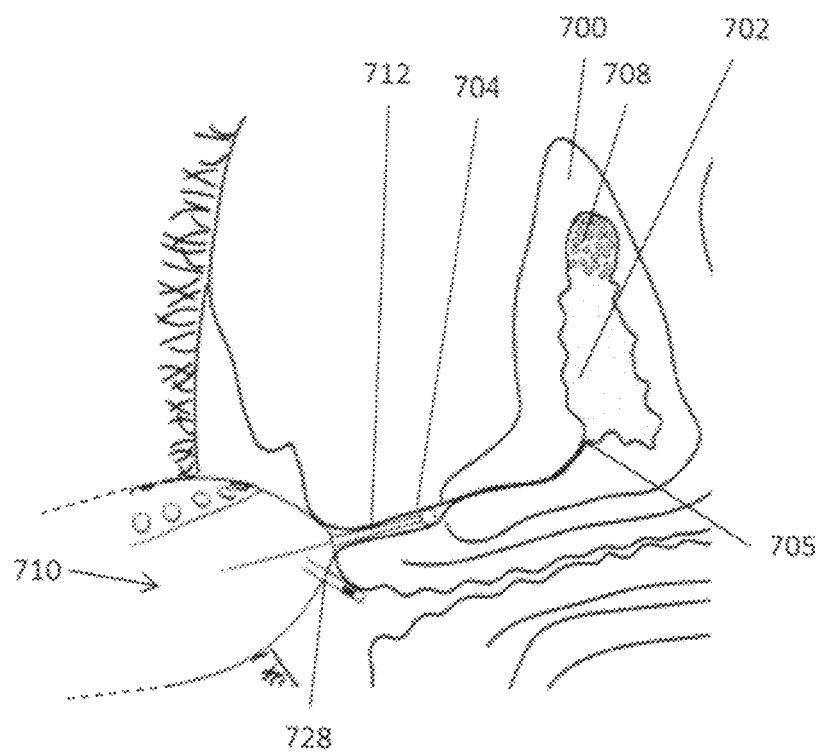
FIG. 7 is a simplified schematic cross sectional view of a treated female, with cushion material in a bladder, according to some embodiments of the invention.

FIG. 7 is a simplified schematic cross sectional view of a treated female, with cushion material 708 in a bladder 700, according to some embodiments of the invention. In some embodiments, when introduction of material ceases, the sphincter muscles close or collapse at least a portion of urethra 704, for example preventing cushion material in the bladder and/or material introduced into the urethra from escaping.

In some embodiments, cushion material 708 is less dense than urine, and moves within the bladder under gravity, for example, rising from an urethral opening to the bladder 705 (e.g. if the female is lying down, introduced material rises from urethral bladder opening 705 to the cushion material 708 position illustrated in FIG. 7). In some embodiments, cushion material 708 increases a volume and/or changes a shape of bladder 700, as illustrated in a change in the bladder shape from FIG. 6B to FIG. 7.

Figure 8:
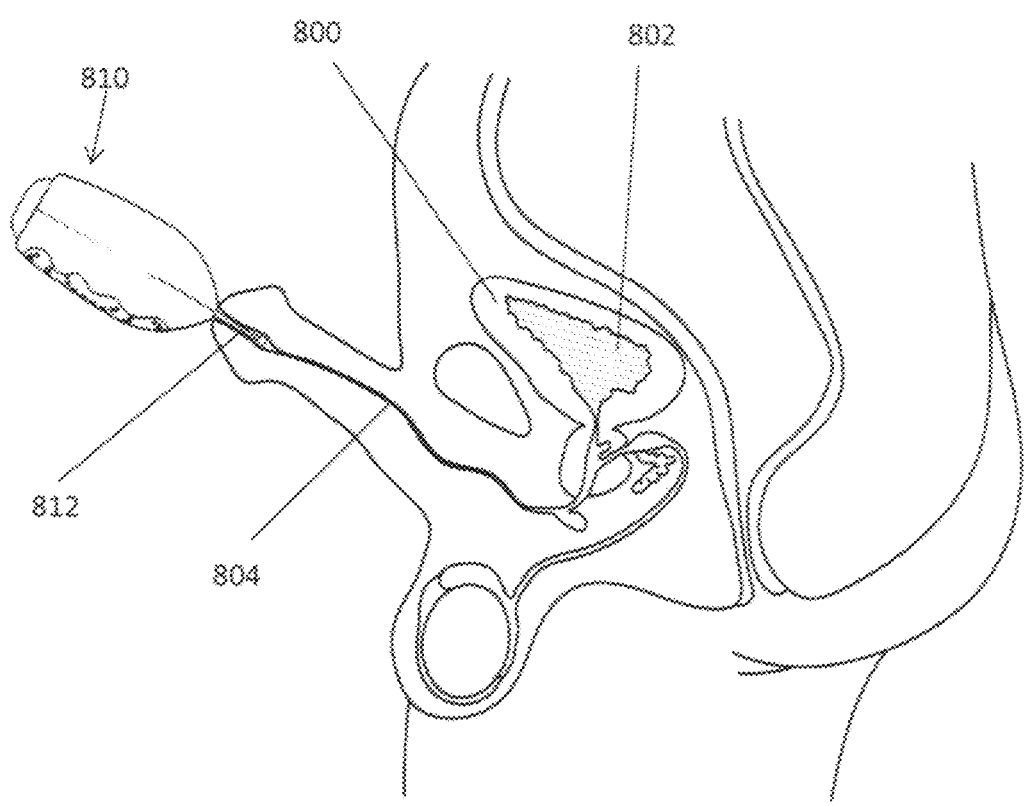
FIG. 8 is a cross sectional view of a male and is a simplified schematic side view of a device, with a portion of the device inserted into a urethra of the male, according to some embodiments of the invention.

FIG. 8 is a cross sectional view of a male and a simplified schematic side view of a device 810, with a portion of the device inserted into a urethra 804 of the male, according to some embodiments of the invention.

Figure 9:
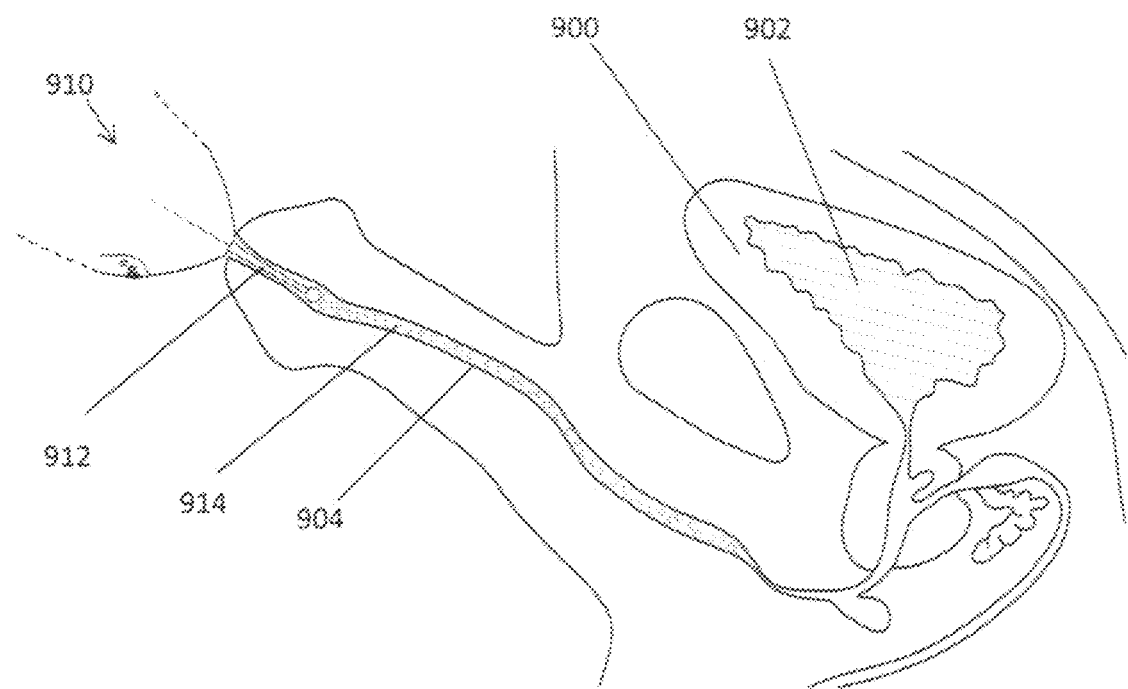
FIG. 9 is a cross sectional view of a male and simplified schematic side view of a portion of a device introducing material into a urethra of the male, according to some embodiments of the invention.

FIG. 9 is a cross sectional view of a male and simplified schematic side view of a portion of a device 910 introducing material 914 into a urethra 904 of the male, according to some embodiments of the invention. For clarity, introduced material 914 is illustrated as fluid including bubbles. In some embodiments, material 914 is introduced through the nozzle 912, when nozzle 912 is positioned inside urethra 904. In some embodiments, a pressure of introduced material opens the urethra, in FIG. 9 the urethra is partially opened by insertion of nozzle 912 and partially opened by pressure of introduced material 914. In some embodiments, at least a portion of material 614 introduced into urethra 904 travels along urethra 904, into bladder 900.

Figure 10:
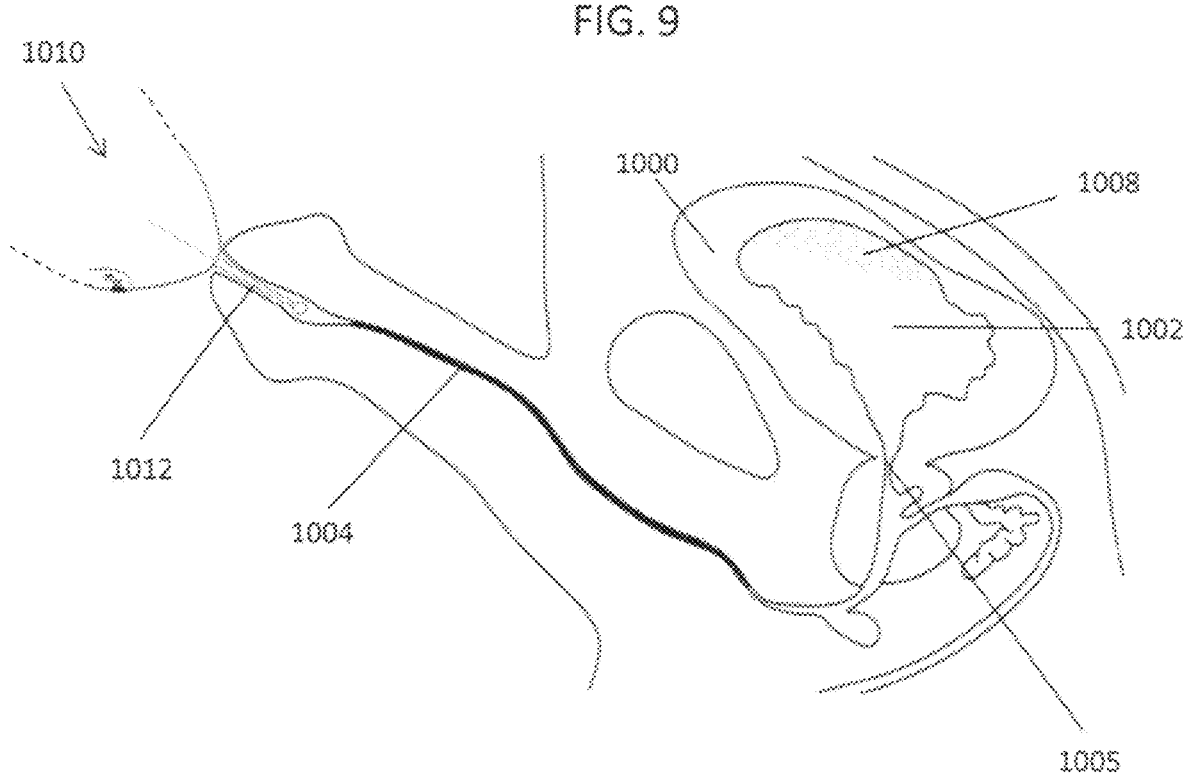
FIG. 10 is a simplified schematic side view of a portion of a device and a cross sectional view of a male body after introduction of material, according to some embodiments of the invention.

FIG. 10 is a simplified schematic side view of a portion of a device 1012 and a cross sectional view of a male body after introduction of material, according to some embodiments of the invention. Material introduced through urethra 1004 is inside bladder 1000, forming cushion material 1008. In some embodiments, cushion material 1008 is less dense than urine 1002, and moves within bladder 1000 under gravity, for example, rising from an urethral opening into the bladder 1005 (e.g. if the male is standing, rising from urethral bladder opening 1005 to the cushion material 1008 position illustrated in FIG. 7). In some embodiments, cushion material 1008 increases a volume and/or changes a shape of bladder 1000, as illustrated in a change in the bladder from FIG. 9 to FIG. 10.

Exemplary Seal—Inserted Nozzle

In some embodiments, urethral flesh seals against and/or around a part of the nozzle, the seal potentially preventing, or reducing escape of introduced material through the urethral opening. In some embodiments, a part of the nozzle is shaped and/or sized to provide and/or enhance a seal between the urethra and the nozzle.

Referring to FIG. 13A, in some embodiments, nozzle 1312 includes a portion of larger cross sectional area 1313. In some embodiments, the nozzle portion of larger cross section area is at a nozzle tip 1313. Alternatively or additionally, in some embodiments, a portion of larger cross sectional area is disposed at a point along a length of nozzle 1312 (e.g. disposed such that, when a part of nozzle 1312 is inserted into urethra 1304, the larger cross sectional area portion plugs the urethral opening, e.g. larger cross sectional area portion is up to 0.5 cm from a nozzle tip, 0.5-1 cm from a nozzle tip or more than 1 cm from a nozzle tip).

Figure 13B:
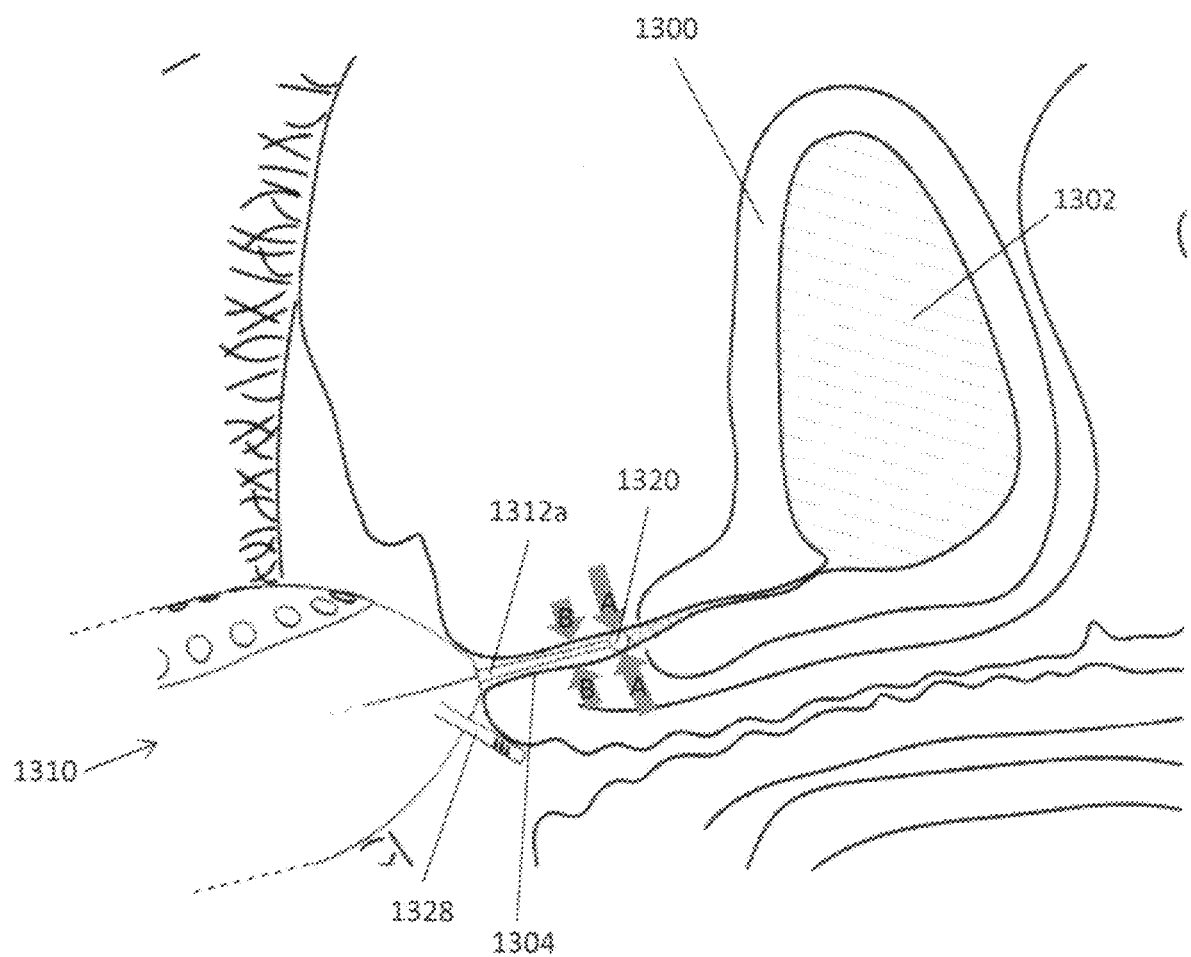
FIG. 13B is a simplified cross sectional view of a nozzle including a sealing portion, inside a female urethra, according to some embodiments of the invention.

In some embodiments, a seal is formed by a higher pressure of the urethra on a part of the inserted nozzle. FIG. 13B is a simplified cross sectional view of a nozzle including a sealing portion 1320, inside a female urethra, according to some embodiments of the invention. Forces A on sealing portion 1320 are higher than forces B on the nozzle 1312. In some embodiments, sealing portion 1320 includes a larger cross sectional area than a body of nozzle 1312a. For example, in some embodiments, sealing portion 1320 includes a rounded shape, as illustrated in FIG. 13B.

Exemplary Embodiment—Nozzle Placed Over Urethra

Figure 17A:
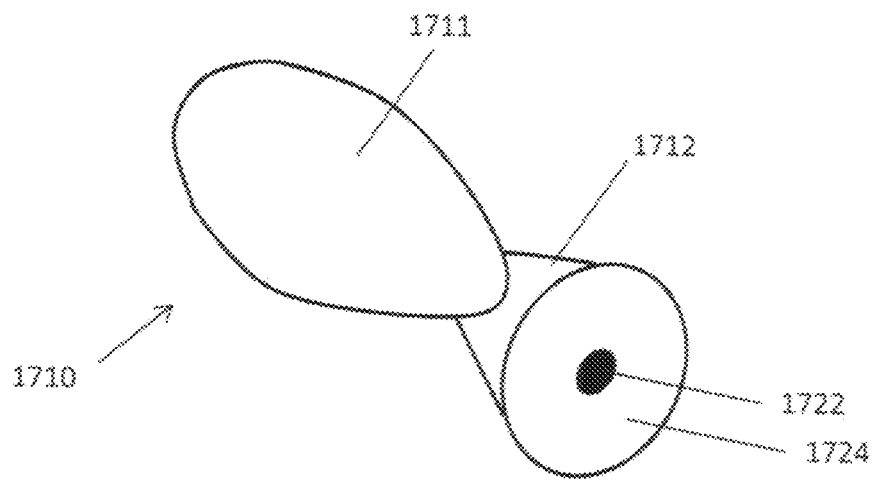
FIG. 17A is a simplified schematic side view of a device, according to some embodiments of the invention.
Figure 17B:
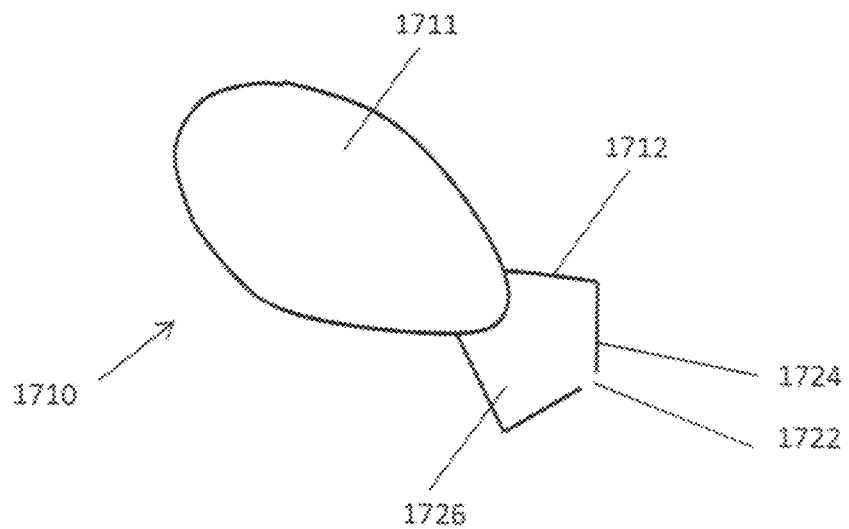
FIG. 17B is a simplified schematic cross sectional view of a device, according to some embodiments of the invention.

In some embodiments, the device nozzle is placed over the urethra. FIG. 17A is a simplified schematic side view of a device 1710, according to some embodiments of the invention. FIG. 17B is a simplified schematic cross sectional view of a device 1710, according to some embodiments of the invention. In some embodiments, device 1710 includes a device body 1711 and a nozzle 1724.

Exemplary Seal—Nozzle Placed Over Urethra

In some embodiments, a part of the nozzle seals against external flesh/skin of the user. In some embodiments, pressure exerted by the user on the device seals the nozzle against user flesh (e.g. flesh surrounding the urethra). In some embodiments, nozzle 1712 is pressed against user skin at the urethral opening, with an outlet 1722 of nozzle over the urethra. In some embodiments, the nozzle is soft and/or rounded enough such that the nozzle forms a seal with flesh around the user urethra without cutting or damaging user flesh.

In some embodiments, the nozzle is lubricated and/or coated (using e.g. water, K-Y Jelly®, Surgilube®) before use, for example, to assist in sealing the device against user tissue.

In some embodiments, for example, upon an initiation of material, pressure of material inside nozzle 1726 is sufficiently high to open the urethra from the urethral opening, and/or for material from device 1710 to enter the urethra.

In some embodiments, a nozzle outlet is located on a protruding portion of the nozzle. For example, in some embodiments, a nozzle includes a protruding cone shape 1724 with outlet 1722 at the peak of the cone (e.g. as illustrated in FIG. 17B). In some embodiments, a protruding outlet 1722 assists contacting outlet 1722 at the urethral opening and/or forming of a seal between nozzle 1724 and user flesh around the urethra.

Figure 18:
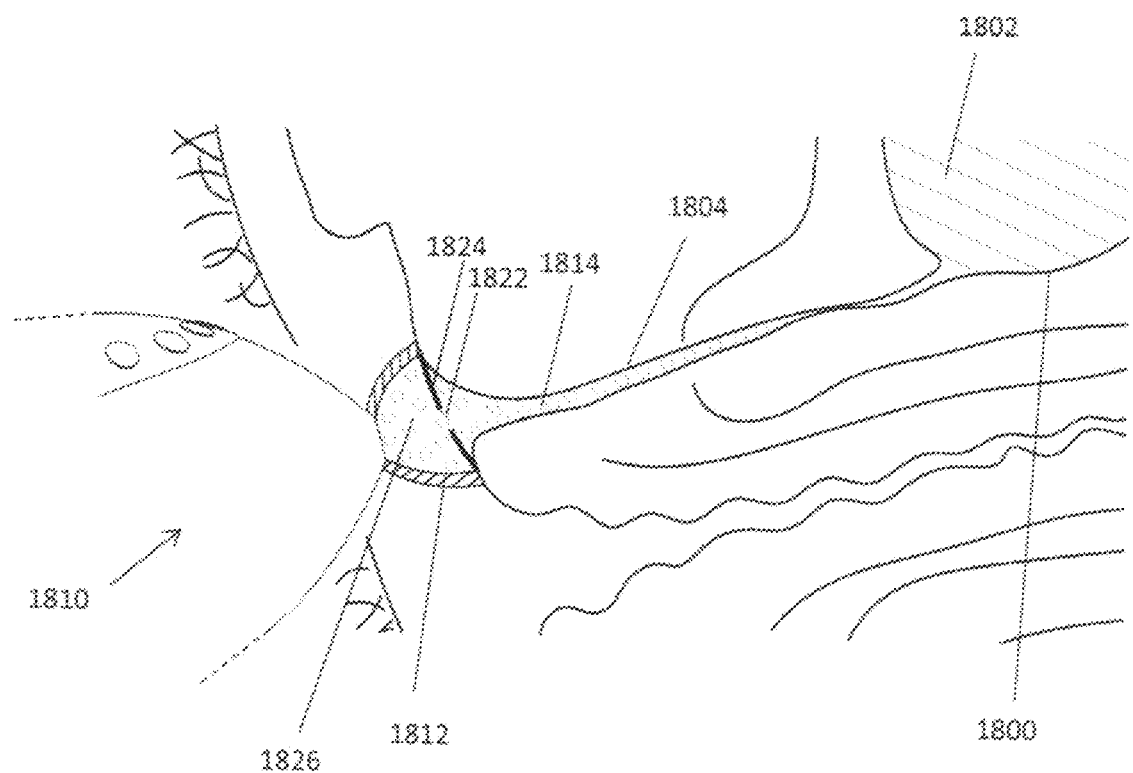
FIG. 18 is a simplified schematic side view of a device and a cross sectional view of a female where the nozzle is introducing material into a urethra of the female, according to some embodiments of the invention.

FIG. 18 is a simplified schematic side view of a device 1810 and a cross sectional view of a female where the nozzle is introducing material into a urethra 1804 of the female, according to some embodiments of the invention.

Figure 19:
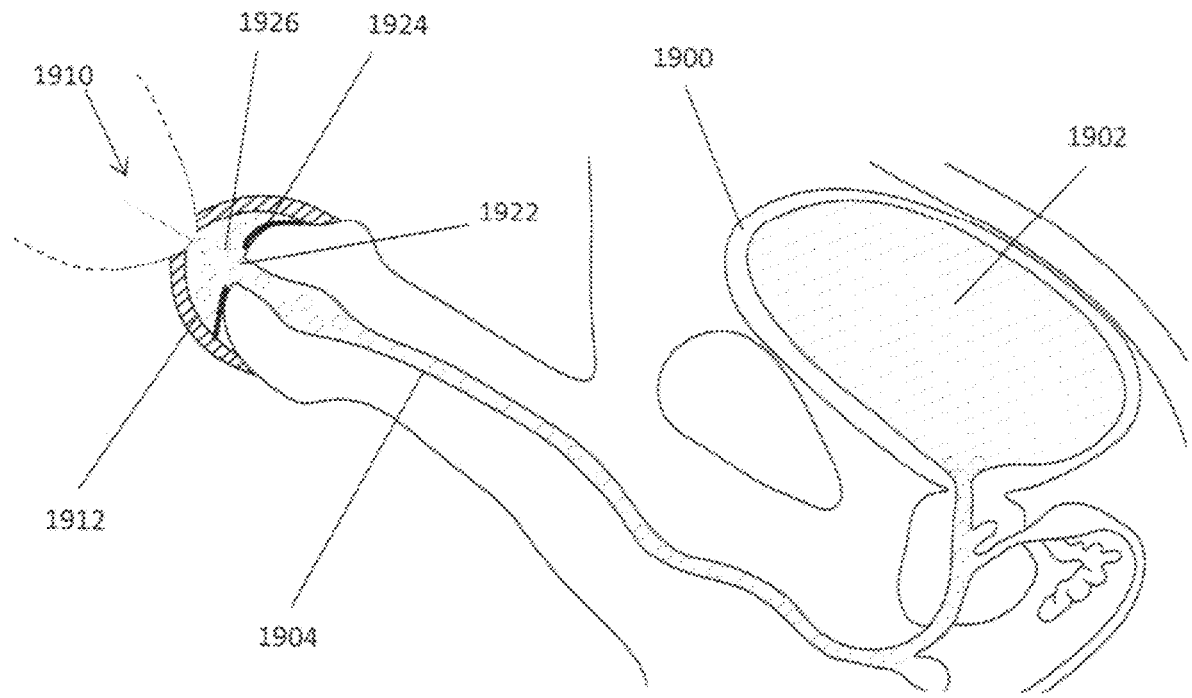
FIG. 19 is a simplified schematic side view of a device and a cross sectional view of a male where the nozzle is introducing material into a urethra of the male, according to some embodiments of the invention.

FIG. 19 is a simplified schematic side view of a device 1910 and a cross sectional view of a male where the nozzle is introducing material into a urethra 1904 of the male, according to some embodiments of the invention.

In some embodiments, a nozzle forms more than one seal against user flesh, for example, as illustrated in FIG. 19, a first outer seal is formed by a nozzle outer portion 1912 against an outer contour around the urethra and a second seal is formed by a nozzle inner portion 1924 against an inner contour around the urethra. In some embodiments, an outer seal secures the nozzle to user flesh and an inner seal resists escape of material.

In some embodiments, a nozzle forms a seal with said urethra and with user flesh around the urethra. In some embodiments, a portion of a nozzle is inserted into said urethra (optionally not forming a seal with the urethra, e.g. nozzle is much smaller in cross section than the urethra) and the nozzle forms a seal with user flesh around the urethra.

In some embodiments, a nozzle includes a concave portion 1924, for example, to provide a seal against user flesh.

In some embodiments, the nozzle deforms or changes shape when in position at a user urethra. For example, in some embodiments, a cone shaped nozzle portion (e.g. nozzle portion 1724 is cone shaped as illustrated in FIG. 17B) is inverted when the device is in position at a user urethra for dispensing.

In some embodiments, a nozzle outlet is larger in cross section than the user urethra (e.g. nozzle outlet 1822 in FIG. 18).

Exemplary Device—Inserted Nozzle

FIG. 21A is a simplified schematic of a side view of a device 2110, according to some embodiments of the invention. FIG. 21B is a simplified schematic of a top view of a device, according to some embodiments of the invention. FIG. 21C is a simplified schematic of a bottom view of a device, according to some embodiments of the invention. FIG. 21D is a simplified schematic of a front view of a device, according to some embodiments of the invention.

Exemplary Handheld Device

In an exemplary embodiment, a device for treatment of SUI is sized to be hand held.

In some embodiments a device is dimensioned (e.g. a device length, a maximum device extent) and/or is a suitable weight such that a user can comfortably hold the device and/or direct the device nozzle to the user urethra.

In some embodiments, a maximum device extent (a largest dimension of the device) is up to 30 cm or up to 25 cm or up to 15 cm or up to 10 cm. In some embodiments, a device is approximately 1-40 cm long, or 5-25 cm long, or 7-20 cm long. In some embodiments, a device body is 0.5-20 cm wide, or 1-15 cm wide, or 3-10 cm wide. In some embodiments, a device body is 0.5-20 cm deep, or 1-15 cm deep, or 3-10 cm deep. In some embodiments, a device body is approximately cylindrical and is 0.5-20 cm in diameter, or 1-15 cm in diameter, or 3-10 cm in diameter.

In some embodiments, a device nozzle has an adjustable length, e.g. the device nozzle is telescopic, e.g. the device nozzle screws in and/or out of the device body.

In some embodiments, a weight of the device is less than 500 g, or less than 300 g, or less than 100 g, or less than 50 g, or less than 20 g.

Alternatively or additionally, in some embodiments, a portion of a device is handheld, for example, in some embodiments, a device nozzle is sized to be hand held.

In some embodiments, device 2110 includes one or more grip element 2136, for example, to provide an indication of correct hand holding of device 2110, for example, to assist a user in gripping the device.

In some embodiments, grip element 2136 is disposed on part of the device, such that when a user grasps the device such that the grip element is in contact with a user's fingers and/or palm, the device is orientated for nozzle insertion. For example, a user grasping device 2010 with grip element 2136 in contact with user fingers and/or palm, holds device 2010 with a top surface (e.g. mirror) of a positioning element 2128 (positioning element described in more detail below) facing in the superior direction.

In some embodiments, grip element 2136 includes one or more non-slip and/or textured surface part (e.g. rubber), for example, to prevent device 2110 from slipping from a user's grasp. In some embodiments, grip element 2136 includes one or more rubber pad 2138.

Exemplary Correct Insertion, Positioning

Exemplary Mechanical Positioning Element

In some embodiments, a user positions a device onto and/or into the user's urethra.

In some embodiments, the device includes a positioning element which is placed onto and/or into a part of the user's body (e.g. in the vagina, in the anus, on the leg) to assist in aligning the nozzle with the urethral opening. Returning now to FIG. 6A, device 610 includes a positioning element 628.

In some embodiments, during insertion of nozzle 612 into the urethra, guiding positioning element 628 towards the vagina assists in positioning the nozzle tip in the vicinity of and/or at the urethral opening: In some embodiments, when nozzle 612 is in position inside urethra 604, positioning element 628 rests inside and/or at the entrance to the vagina.

In some embodiments, positioning element 628 is angled such that, for example, during insertion of nozzle 612 into the urethra, guiding positioning element 628 into the vagina assists in inserting nozzle 612 into the urethra (e.g. the angle of movement of the nozzle is aligned to the angle of the urethra).

Exemplary Cue Positioning Element

In some embodiments, one or more positioning element provides visual and/or audio clues for positioning the device.

In some embodiments, one or more positioning element includes an indicator of a distance of the nozzle from a target position (e.g. distance between a nozzle tip the urethral opening).

In some embodiments, one or more positioning element includes a visual element (e.g. mirror and/or camera), providing visual clues, for example, as to the distance between the nozzle and the urethral opening.

Figure 20A:
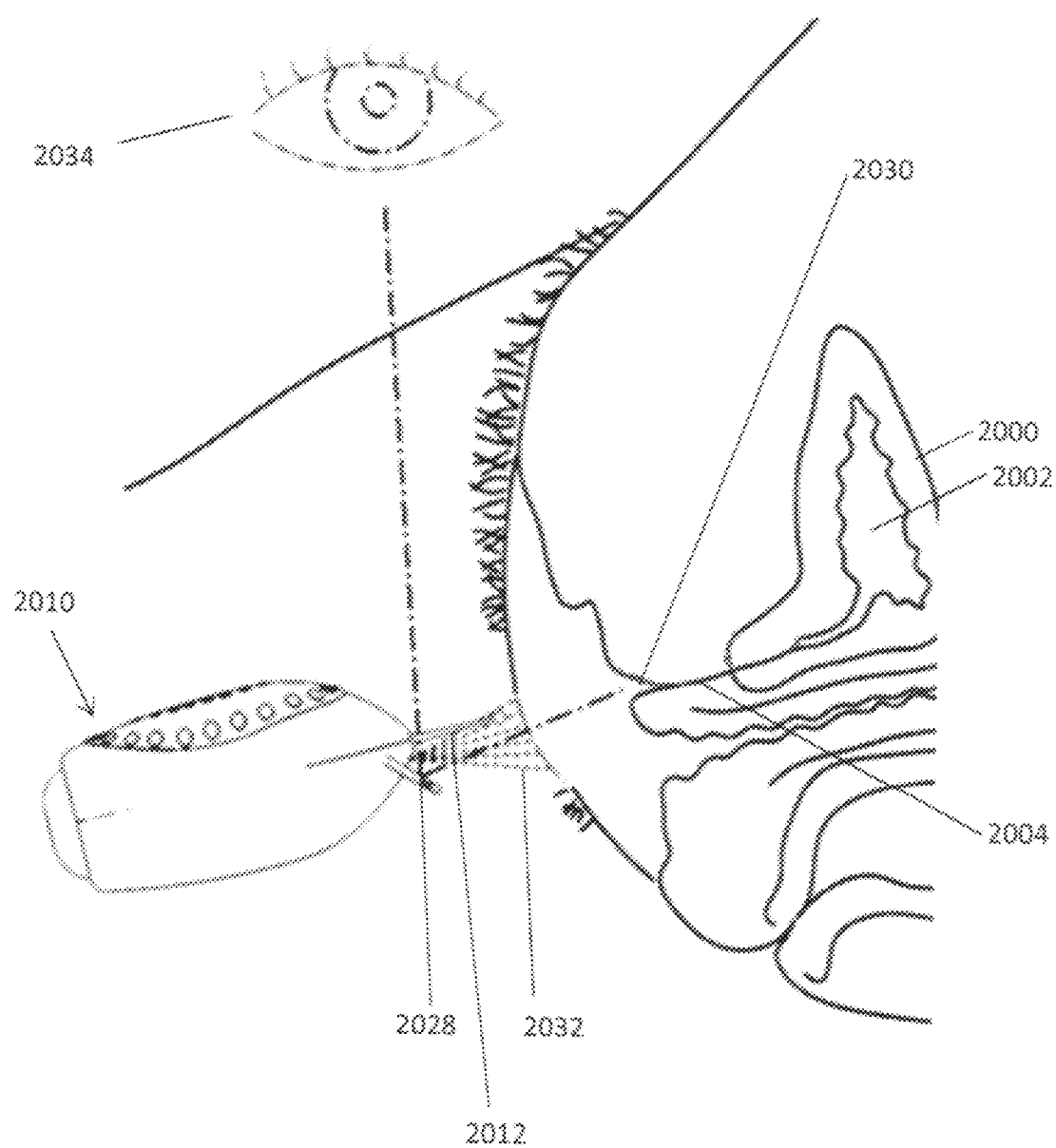
FIG. 20A is a simplified schematic of a side view of a device including a positioning element and a cross sectional view of a user, according to some embodiments of the invention.

FIG. 20A is a simplified schematic of a side view of a device 2010 including a positioning element 2028 and a cross sectional view of a user, according to some embodiments of the invention. In some embodiments, positioning element 2028 includes a reflective surface (e.g. a mirror). For example, in FIG. 20A, mirror positioning device 2028 and nozzle 2012 are angled such that when nozzle 2012 is generally directed towards a urethral opening 2030 (e.g. pointing to within 1 cm of the urethral opening), positioning device 2028 shows a user 2034 a position of nozzle 2012 with respect to urethral opening 2030.

Referring now to FIG. 21A, in some embodiments, positioning element 2128 (e.g. to a device body 2111) is adjustable, for example by a user e.g. so that the user can adjust the positioning element to a user anatomy and/or so that the user can adjust a visual positioning element (e.g. mirror) such that the user can view the nozzle and/or urethral opening in the mirror. In some embodiments, positioning element 2128 includes a pulling grip 2148 (e.g. one or more rubber grip) which assists the user in pivoting and/or moving the positioning element.

Optionally, in some embodiments, the device includes one or more element which confirms that the device is in position, for example, inserted sufficiently deep into the urethra. In some embodiments a depth to which the nozzle is inserted into the urethra is measured, for example, by a sensor. In some embodiments, feedback is provided for example, to a user (e.g. through a user interface) as to nozzle depth. In some embodiments, dispensing of material is only upon confirmation that the nozzle is inserted sufficiently into the urethra. For example, an automated controller only dispenses material upon receiving confirmation (e.g. from a sensor).

In some embodiments, the nozzle includes one or more marking to guide a user in correct insertion, for example, the user inserts the nozzle such that a marking is approximately at the urethral opening.

Optionally, in some embodiments, the device includes one or more element which confirms that introduced material, and/or a sufficient proportion of introduced material remains within the urinary system and/or enters the bladder. In some embodiments, the device includes an element (e.g. gas leak sensor, pressure sensor) which provides feedback, optionally during and/or before dispensing. In some embodiments, the element confirms that an acceptable level of dispensed material is escaping, e.g. out of the urethral opening.

Exemplary Illumination

In some embodiments, device includes an illumination element, for example illumination element 2146, FIG. 21D (e.g. LED, light bulb) for example, for illumination 2032 of a target area for the nozzle (e.g. urethral opening 2032, area around the urethral opening). A potential benefit of a device including an illumination element is ability to use the device in low lighting (e.g. public bathroom).

In some embodiments, illumination element 2146, illustrated in FIG. 21D is in close proximity to nozzle 2120. For example, in some embodiments, an illumination element is disposed on a device body up to 1 mm away from, or up to 5 mm away from, or up to 20 mm away from the nozzle, as measured on the outer surface of the device body. In some embodiments, illumination element directs light towards a nozzle tip. A potential benefit of a device with an illumination element disposed in close proximity to a nozzle and/or an illumination element directing light towards a nozzle tip is improved nozzle positioning accuracy and/or improved ease of nozzle positioning and/or insertion, for example as contrast lighting improves positioning.

Figure 25:
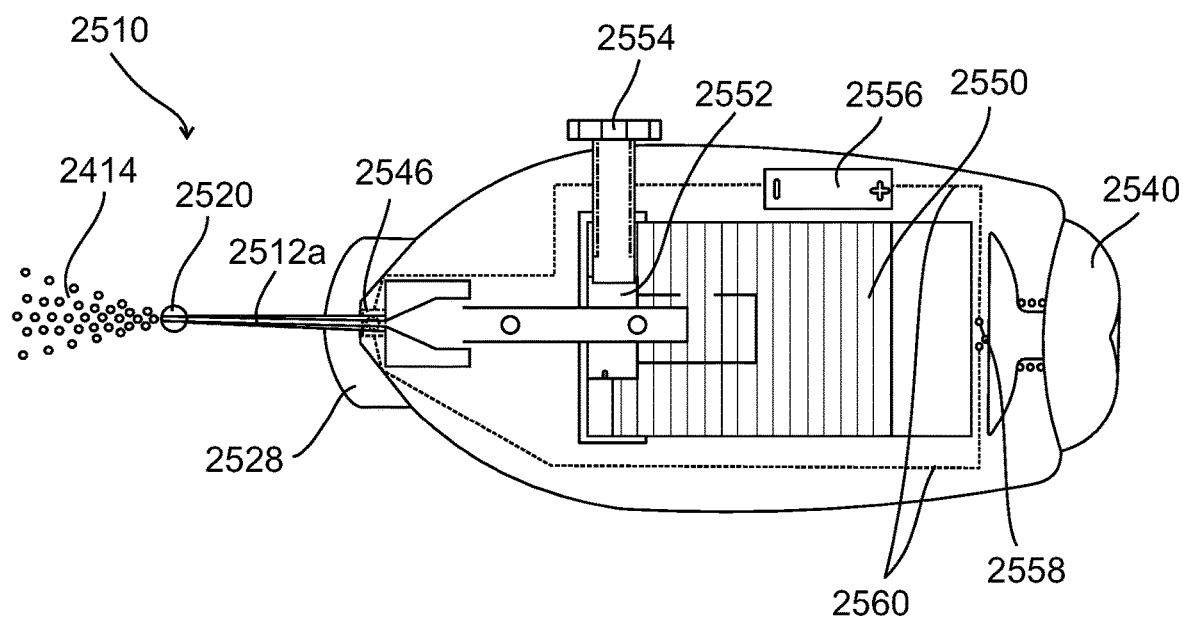
FIG. 25 is a simplified schematic cross sectional view of a device including adjustable volume dispensing according to some embodiments of the invention.

Referring now to FIG. 25, in some embodiments, an illumination element 2546 is at least partially powered by a battery 2556. In some embodiments, illumination element 2546 is switched on by closing a switch 2558 (e.g. by depression of a button 2540) and is optionally connected by wires 2560 to battery 2556 and illumination element 2546.

Exemplary Nozzle for Insertion into the Urethra

In some embodiments, nozzle 2112 is sufficiently rigid to mechanically open the urethra under pressure applied by a user. In some embodiments, the nozzle is sufficiently rigid such that a user inserts the nozzle into the urethra by holding and/or directing a device body, to which the nozzle is coupled.

In some embodiments, nozzle 2112 is flexible enough to follow a contour of a user urethra during insertion.

In some embodiments, the nozzle is elongate. In some embodiments, a nozzle length is 0.1-10 cm, or 0.5-5 cm.

In some embodiments, the nozzle has constant cross section along a nozzle length. In some embodiments, the nozzle has a tapered cross section along a nozzle length, for example with a larger cross section at a nozzle connection to a device body.

In some embodiments, the nozzle includes an approximately circular cross section. In some embodiments, a nozzle cross section is 5 mm-12 mm in diameter. In some embodiments, a nozzle cross sectional area is 20 $mm^2$ to 110 $mm^2$.

In some embodiments, the nozzle is made of silicone rubber. Other suitable materials include, for example, materials commonly used for catheters, e.g. polyurethane, polyethylene terephthalate (PETE), latex, thermoplastic elastomers.

In some embodiments, a nozzle is a separate component. In some embodiments, a different and/or clean and/or sterile nozzle is used for each treatment. In some embodiments, a nozzle includes pre-applied lubricant and/or medication, e.g. in some embodiments, a nozzle cap includes a lubricant reservoir. In some embodiments, the nozzle is lubricated with hormone medication. In some embodiments, hormone medication is female hormone medication, for example, to treat hormone related urethral weakness, e.g. weakness associated with menopause.

In some embodiments, the device is stored detached from the nozzle, for example, for compactness.

Figure 22A:
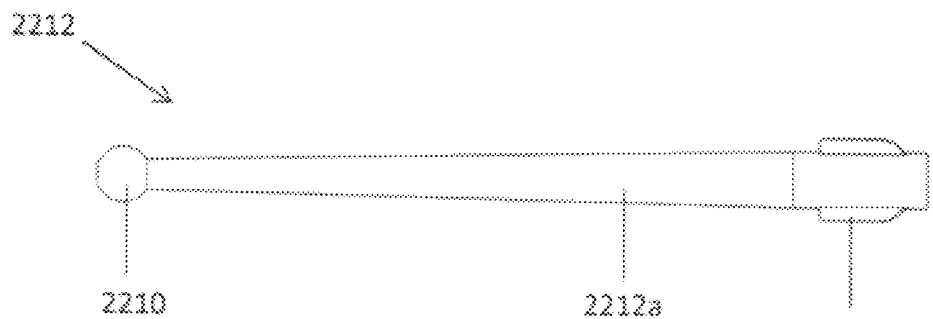
FIG. 22A is a simplified schematic side view of a nozzle including a latch attachment, according to some embodiments of the invention.
Figure 22B:
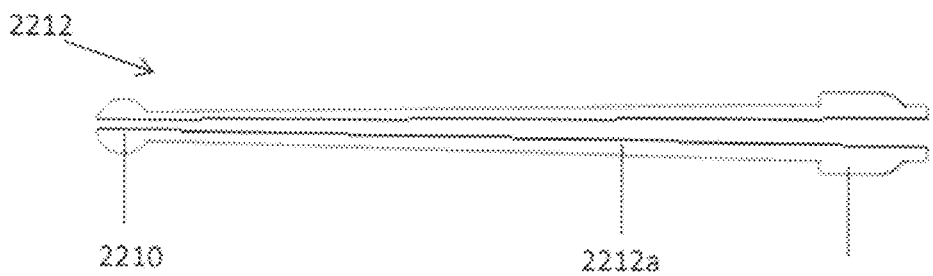
FIG. 22B is a simplified schematic cross sectional view of a nozzle, according to some embodiments of the invention.

In some embodiments, the nozzle latches onto a body of the device. FIG. 22A is a simplified schematic side view of a nozzle including a latch attachment, according to some embodiments of the invention. FIG. 22B is a simplified schematic cross sectional view of a nozzle, according to some embodiments of the invention.

Figure 23A:
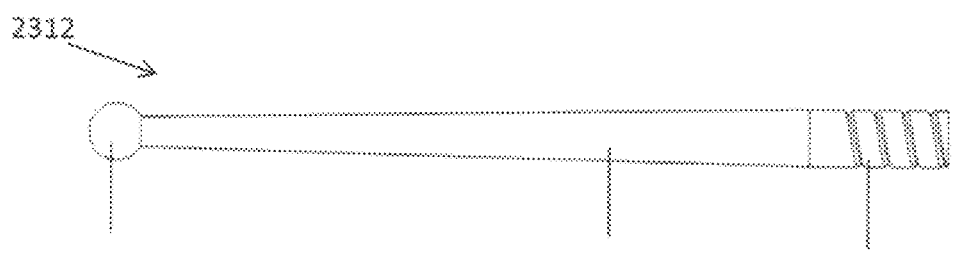
FIG. 23A is a simplified schematic side view of a nozzle including a screw attachment, according to some embodiments of the invention.
Figure 23B:
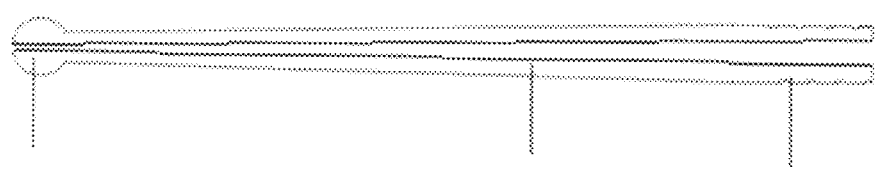
FIG. 23B is a simplified schematic cross sectional view of a nozzle including a screw attachment, according to some embodiments of the invention.

In some embodiments, the nozzle screws onto a body of the device, according to some embodiments of the invention. FIG. 23A is a simplified schematic side view of a nozzle including a screw attachment, according to some embodiments of the invention. FIG. 23B is a simplified schematic cross sectional view of a nozzle including a screw attachment, according to some embodiments of the invention.

In some embodiments, a nozzle length is adjustable. A potential benefit of an adjustable nozzle length as, for example, more obese users can extend the nozzle such that the user view of a positioning element (e.g. mirror) is unobstructed by the user's stomach. Another potential benefit of adjustable nozzle length is the ability to personalize the nozzle length.

Exemplary Introduction of Material without Contamination

In some embodiments, material is introduced without the flow of material introducing contamination (e.g. dirt, bacteria, for example, from the urethra, skin, on the device, into the urethra and/or bladder) or with the flow of material introducing a minimal amount of contamination.

In some embodiments, a nozzle includes an invert portion normally disposed inside a body of the nozzle (e.g. when the device is not dispensing material). In some embodiments, the invert portion uninverts under pressure of material to be dispensed from the nozzle. Optionally, the invert portion uninverts before material begins to dispense. Optionally, the invert portion increases an extent (e.g. length) of the nozzle during dispensing of material.

Figure 14A:
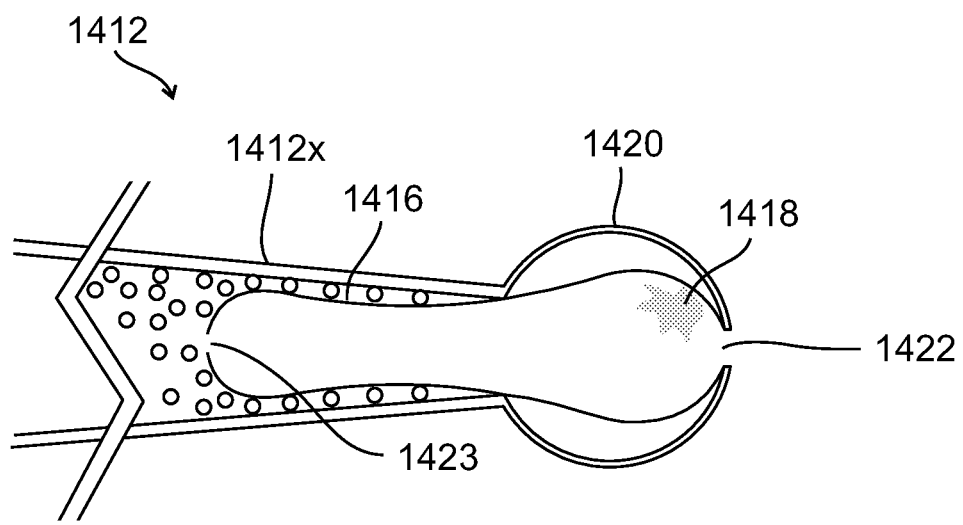
FIG. 14A is a simplified cross-sectional view of part of a device nozzle, when the device is not dispensing material, according to some embodiments of the invention.
Figure 14B:
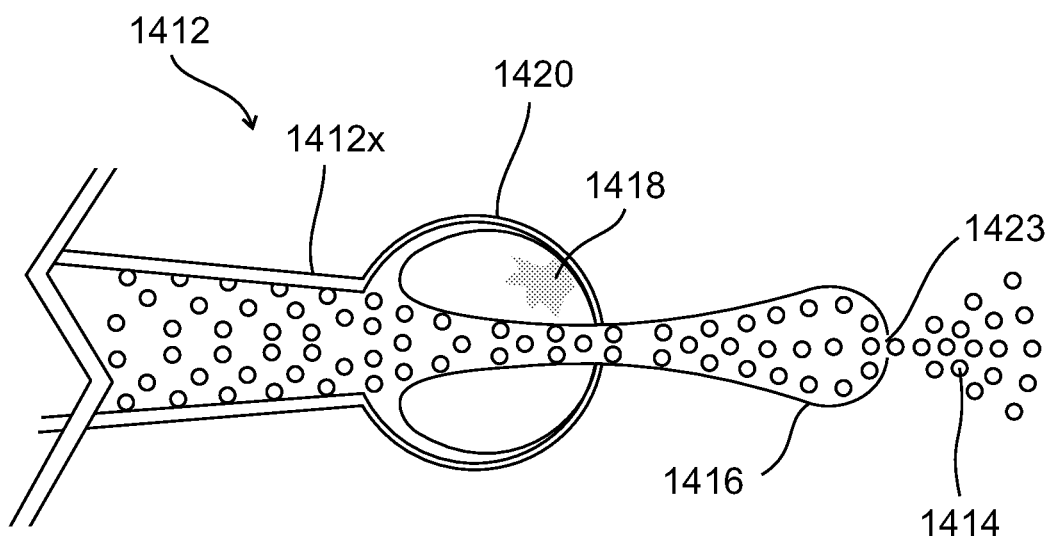
FIG. 14B is a simplified cross-sectional view of part of a device nozzle, when the device is dispensing material, according to some embodiments of the invention.

FIG. 14A is a simplified cross-sectional view of part of a device nozzle 1412, when the device is not dispensing material, according to some embodiments of the invention. FIG. 14B is a simplified cross-sectional view of part of a device nozzle 1412, when the device is dispensing material, according to some embodiments of the invention.

For example, during placing of the device nozzle into the urethra, contamination 1418 may collect on and/or inside nozzle 1412, for example, before insertion and/or during insertion (e.g. mucus, environmental dirt, bacteria). In some embodiments, contamination 1418 enters nozzle 1412 through a nozzle outlet 1422.

In some embodiments, device nozzle 1412 (e.g. device tip) includes an invert portion 1416, which is disposed inside the nozzle (e.g. in an inverted configuration) when the device is not dispensing material, as illustrated in FIG. 14A. In some embodiments, dispensing of material results in uninverting of invert portion 1416, as illustrated in FIG. 14B. In some embodiments, material is dispensed through an invert portion outlet 1423.

A potential benefit of a nozzle including a normally inverted portion which uninverts before and/or during dispensing of material is that contamination 1418 is not in contact with a flow of material, for example, contamination 1418 is less likely to be carried by introduced material 1414 into the urethra and/or bladder.

In some embodiments, after dispensing, invert portion 1416 re-inverts back into nozzle 1412, for example, returning after introduction of material to an inverted configuration inside nozzle (e.g. the configuration illustrated in FIG. 14A). In some embodiments, invert section 1416 is elastic and/or has a shape memory.

In some embodiments, invert portion 1416 is a formed of flexible material, for example, rubber (e.g. silicone rubber).

In some embodiments, an invert section disposed inside the nozzle when the device is not dispensing material uninverts by rolling, for example, under pressure of material to be dispensed.

Figure 15A:
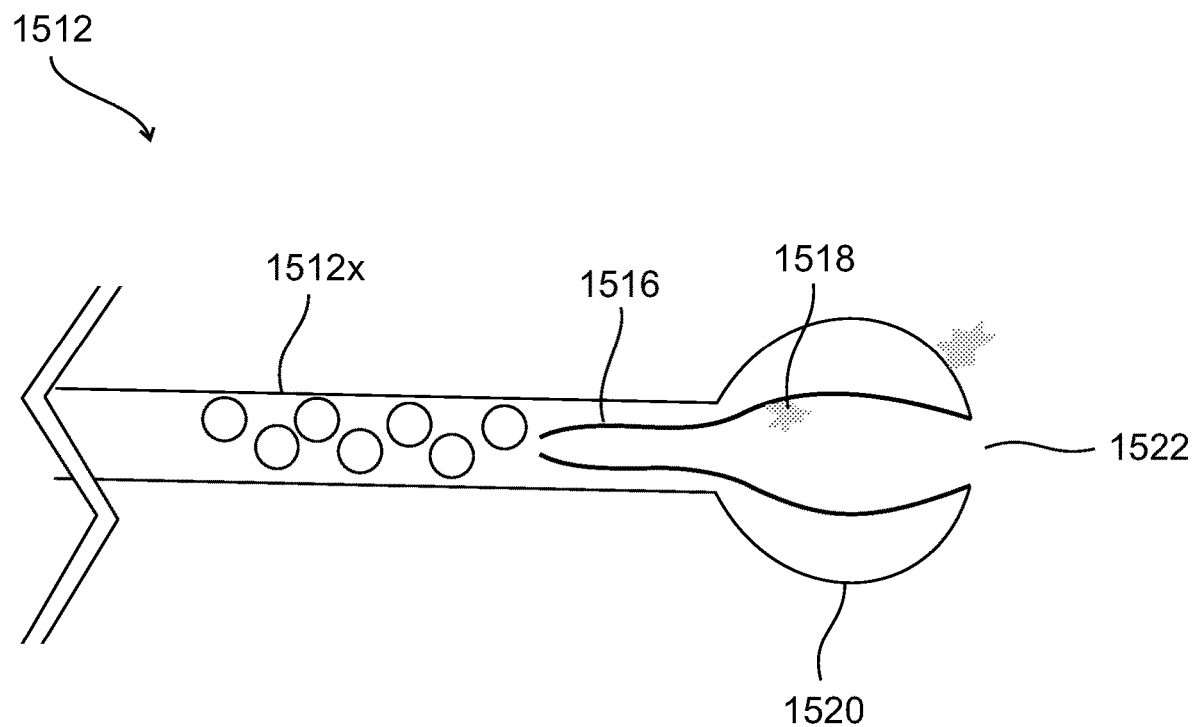
FIG. 15A is a simplified cross-sectional view of part of a device nozzle, including an invert portion, when the device is not dispensing material, according to some embodiments of the invention.
Figure 15B:
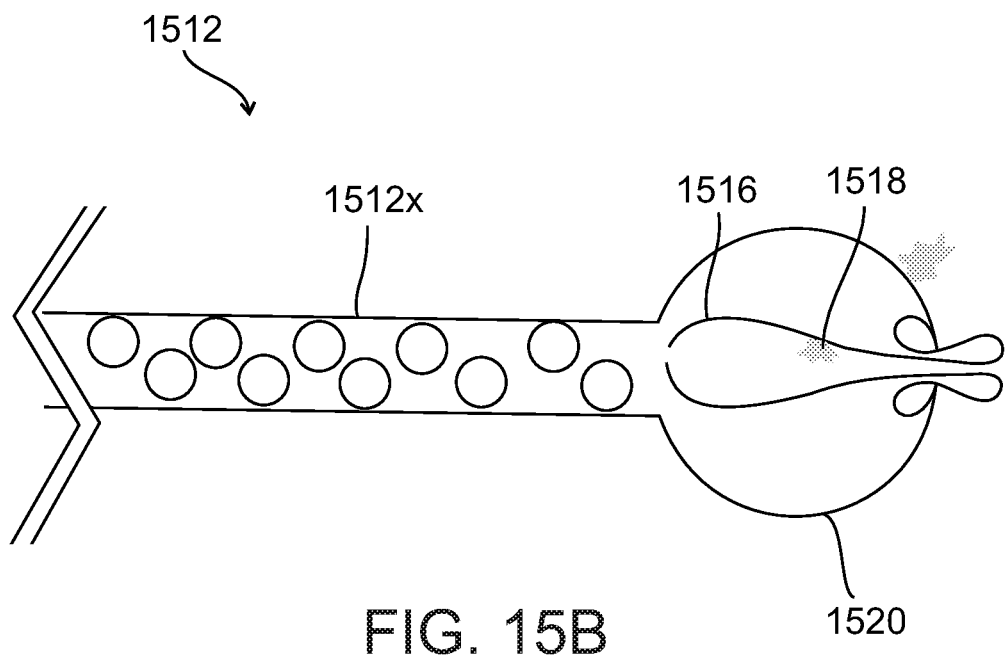
FIG. 15B is a simplified cross-sectional view of part of a device nozzle, during rolling of an invert section, according to some embodiments of the invention.
Figure 15C:
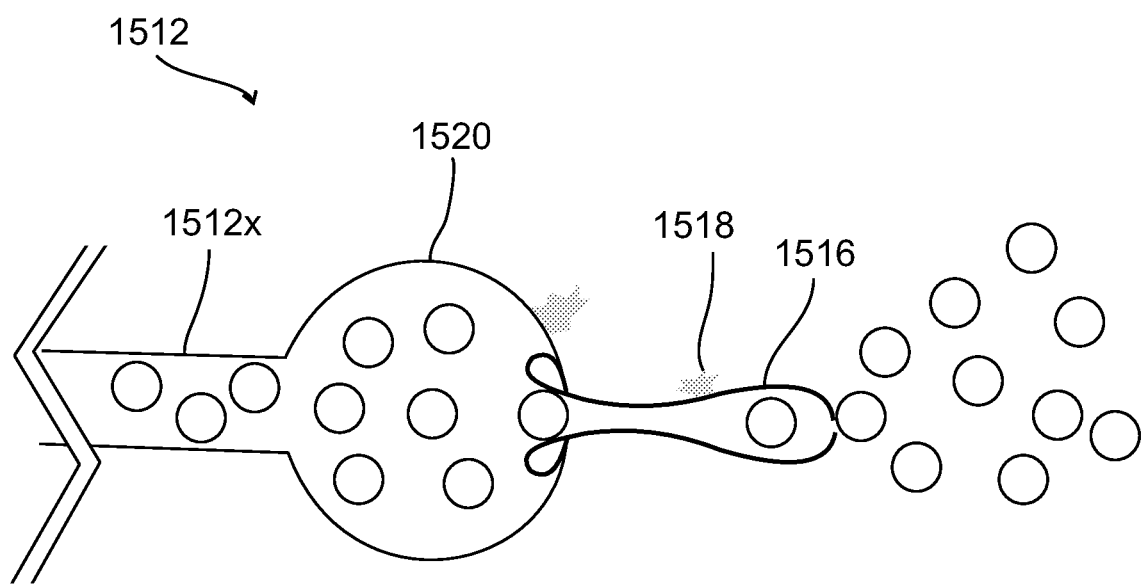
FIG. 15C is a simplified cross-sectional view of part of a device nozzle including an invert section, during dispensing, according to some embodiments of the invention.

FIG. 15A is a simplified cross-sectional view of part of a device nozzle 112, including an invert portion 1516, when the device is not dispensing material, according to some embodiments of the invention. FIG. 15B is a simplified cross-sectional view of part of a device nozzle 1512, during rolling of an invert section 1516, according to some embodiments of the invention. FIG. 15C is a simplified cross-sectional view of part of a device nozzle 1512 including an invert section 1516, during dispensing, according to some embodiments of the invention.

In some embodiments, rolling results in the invert portion closing and/or restriction of the device outlet (as illustrated in FIG. 15B), preventing material from being dispensed (or reducing the amount of material dispensed), before the invert portion unrolls, disposing any contamination away from the flow of material.

Figure 16A:
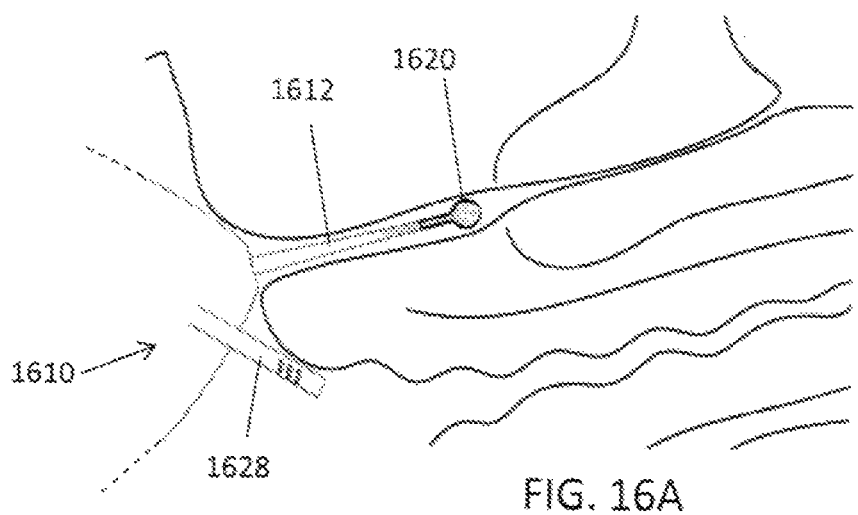
FIG. 16A is a simplified cross sectional view of a nozzle including an invert portion and a cross sectional view of a female where the nozzle is inserted into a female urethra, according to some embodiments of the invention.

FIG. 16A is a simplified cross sectional view of a nozzle 1612 including an invert portion 1620 and a cross sectional view of a female where the nozzle is inserted into a female urethra 1604, according to some embodiments of the invention.

Figure 16B:
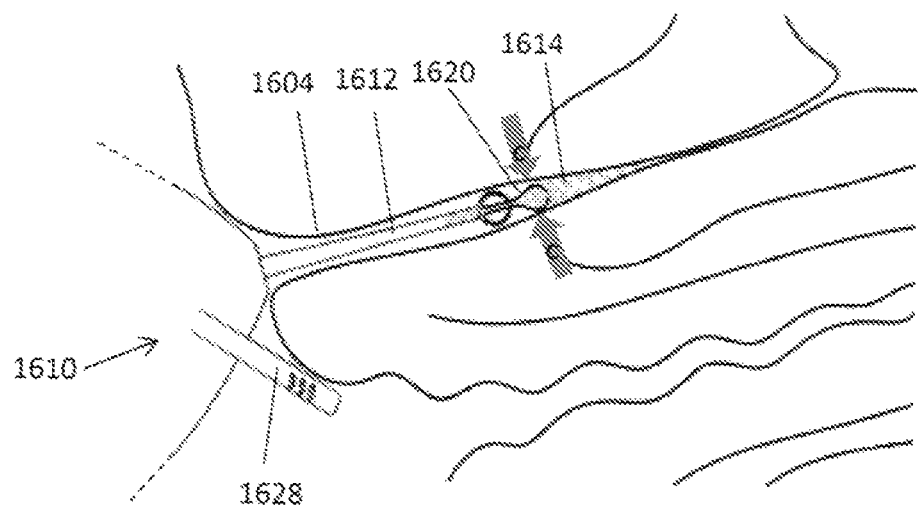
FIG. 16B is a simplified cross sectional view of a nozzle including an invert portion and a cross sectional view of a female where the nozzle is inserted into a female urethra and is introducing material, according to some embodiments of the invention.

FIG. 16B is a simplified cross sectional view of a nozzle 1612 including an invert portion 1620 and a cross sectional view of a female where the nozzle is inserted into a female urethra 1604 and is introducing material 1614, according to some embodiments of the invention. In FIG. 16B introduced material has opened a portion of urethra 1604.

Figure 16C:
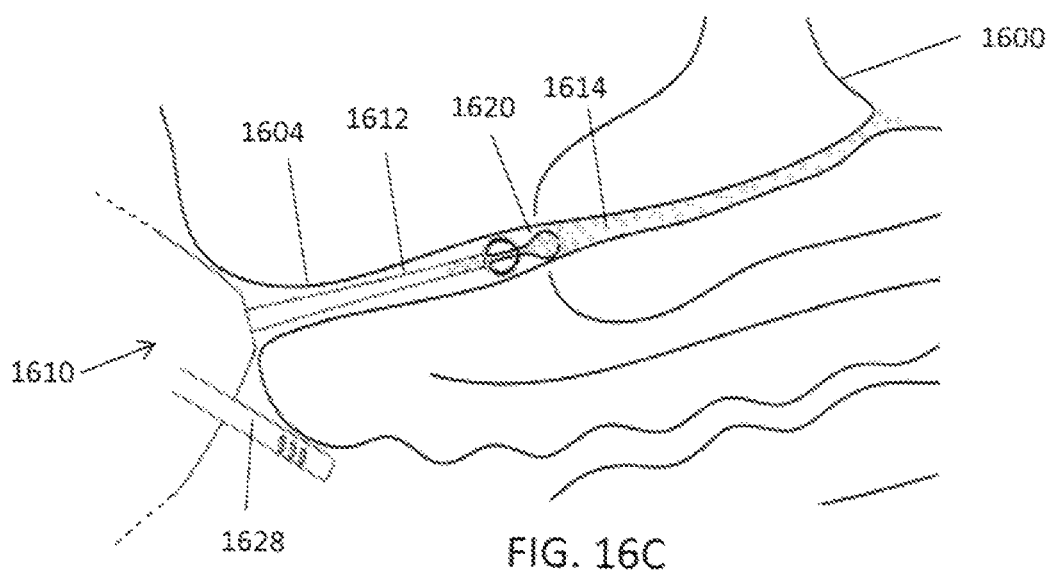
FIG. 16C is a simplified cross sectional view of a nozzle including an invert portion and a cross sectional view of a female where the nozzle is inserted into a female urethra and is introducing material, according to some embodiments of the invention.

FIG. 16C is a simplified cross sectional view of a nozzle 1612 including an invert portion 1620 and a cross sectional view of a female where the nozzle is inserted into a female urethra 1604 and is introducing material 1614, according to some embodiments of the invention. In FIG. 16B introduced material has opened urethra 1604 up to a bladder 1600 and introduced material 1614 is entering bladder 1600.

In some embodiments, a nozzle includes a portion normally disposed inside the nozzle which extends out of the nozzle (e.g. increasing an extent of the nozzle), before and/or during dispensing of material. In some embodiments the portion normally disposed inside the nozzle is optionally flexible and/or soft (e.g. made of rubber, silicone rubber) for example, to avoid abrasion and/or damage to the urethra. In some embodiments, the portion normally disposed inside the nozzle extends outside of the nozzle by unrolling, for example, to reduce friction and/or abrasion of the portion against the urethra. A potential benefit being further introduction of the device into the urethra with potentially less damage to the urethra than caused by introducing a more rigid portion.

Exemplary Material Source

Figure 20B:
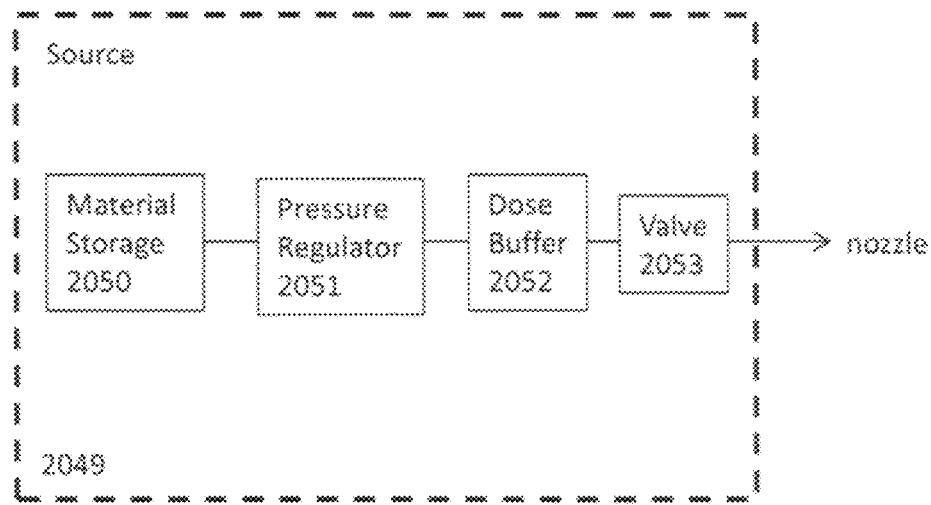
FIG. 20B is a simplified block diagram of a material source, according to some embodiments of the invention.

In some embodiments, introduced material flows from a material source (also herein termed 'source') coupled to a nozzle, through the nozzle. FIG. 20B is a simplified block diagram of a material source 2049, according to some embodiments of the invention. In some embodiments, source 2049 includes a material storage 2050 for storing material. In some embodiments, a flow pathway of material from material storage 2050 to a nozzle is firstly through a pressure regulator 2051 (coupled to material storage 2050) and then through a dose buffer 2052 (coupled to pressure regulator 2051) and then to a valve 2053 (coupled to dose buffer 2052) through which the material flows to the nozzle.

In some embodiments, material storage 2050 includes, for example, a gas canister e.g. storing material at pressures at up to 200 atmospheres or more. In some embodiments, material is stored in material storage 2050 in a different phase e.g. liquid gas.

In some embodiments, for example, as described elsewhere in this document, source 2049 includes a pump and/or an inlet. For example, in some embodiments, material storage 2050 is replaced by a pump and inlet. For example, in some embodiments, a pump coupled to an inlet fills material storage 2050.

Optionally, in some embodiments, a material source 2049 includes a pressure regulator 2052, for example, coupled to the material storage, to regulate (e.g. reduce, modulate) a pressure of material, to a suitable pressure and/or a suitable pressure with time (e.g. pressure which is non-damaging to a urethra before dispensing). Optionally pressure regulator 2052 regulates the pressure of material to the pressure at which the material is dispensed. Alternatively, the pressure is changed further along the flow pathway (e.g. valve 2053 changes the material pressure prior to and/or during dispensing).

Optionally, in some embodiments, material source 2049 includes a dose buffer 2051 for regulating a dose size, which is, for example, loaded with material by material storage 2050. Optionally, dose buffer 2052 has an adjustable capacity and a dose size of dispensed material is regulated by dispensing the material stored in dose buffer 2052.

In some embodiments, material source 2049 includes a valve 2053, for example, for control of dispensing of material. In some embodiments, valve 2053 includes an open and a closed state. In some embodiments, valve opens (and/or closes) gradually, for example to gradually increase a quantity and/or pressure of material dispensed.

Optionally two or more of pressure regulator 2051, dose buffer 2052 and valve 2053 are combined. For example, in some embodiments, a pressure reduction valve includes pressure regulator 2051 and valve 2053.

In some embodiments, an order in the flow pathway of pressure regulator 2051, dose buffer 2052 and valve 2053 is different to that depicted in FIG. 20B. For example, in some embodiments, pressure is regulated after (in the flow pathway) a dose of material is collected (dose buffer 2052 is before pressure regulator 2051 in the flow pathway).

Optionally, in some embodiments, a source includes one or more disposable part. For example, in some embodiments, material storage 2049 includes a removable canister.

Optionally the removable canister includes an internal valve e.g. to prevent material from escaping before the canister is in place in the device and/or a connector to connect the canister to other elements in the source (e.g. pressure regulator 2051).

Optionally, in some embodiments, the source includes one or more refillable part, for example, in some embodiments; material storage 2049 is a refillable canister. For example, in some embodiments, material storage 2049 includes an inlet (and optionally a valve e.g. to prevent material from escaping through the inlet) and material storage 2049 is refilled through the inlet. In some embodiments, material storage 2049 is removed and refilled outside the device. In some embodiments, material storage 2049 is refilled whilst within the device.

In some embodiments, the device is reused for multiple treatments e.g. material storage contains sufficient material for a multiple treatments. Alternatively, in some embodiments, the device is a single use disposable device e.g. material storage contains sufficient material for at least one treatment.

Figure 24:
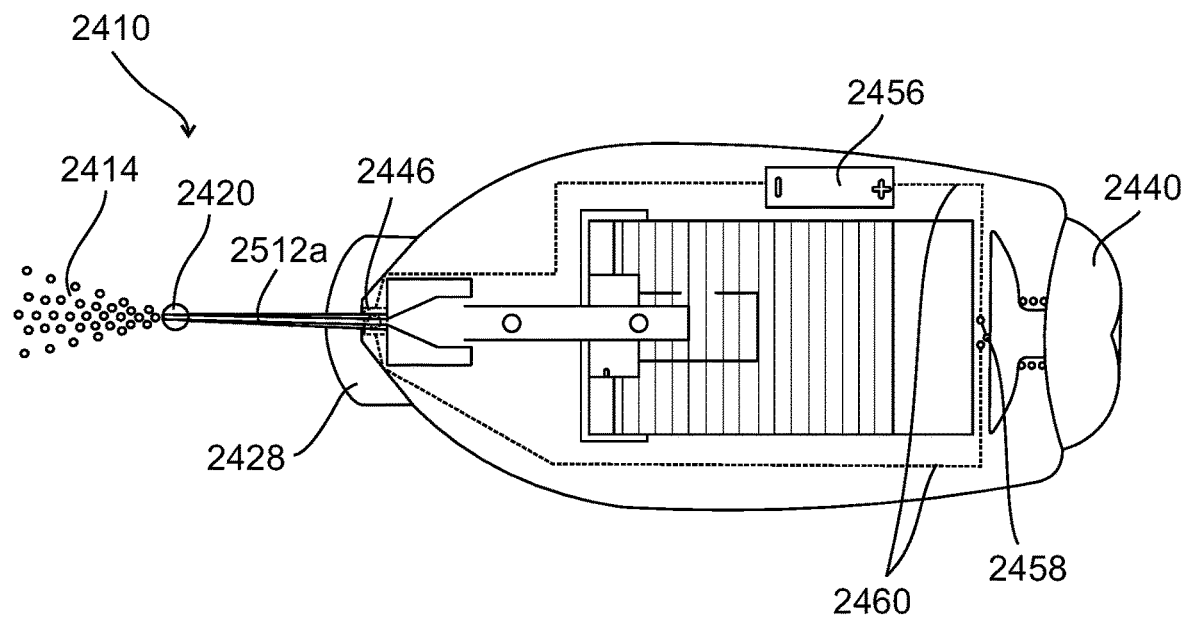
FIG. 24 is a simplified schematic cross sectional view of a device, according to some embodiments of the invention.

FIG. 24 is a simplified schematic cross sectional view of a device, according to some embodiments of the invention. In some embodiments, the device includes a material source, which includes a material storage 2450. In some embodiments, the material source stores material under pressure (e.g. material storage 2450 is a gas canister).

Alternatively or additionally, in some embodiments, the material source includes an inlet and a pump (e.g. for collecting and/or compressing air from the inlet). In some embodiments, ambient air is sucked into the device through the inlet and compressed by the pump, before being dispensed. Optionally, in some embodiments, air collected by the inlet and optionally compressed by the pump is stored (e.g. in a material storage) before dispensing. Optionally, in some embodiments, the material source includes a cleaning element, for example, for cleaning collected ambient air (e.g. a filter).

Exemplary Control

In some embodiments, the device includes a control, for example, for control of flow of material from the source through the nozzle. In some embodiments, the control controls the amount of material dispensed from the source, for example, dispensing non-damaging quantities. In some embodiments, the control controls the pressure of material dispensed from the source, for example, dispensing material at non-damaging pressure.

In some embodiments, a control dispenses an amount of material upon a user initiation e.g. through a user interface (as described in more detail below).

In some embodiments, the device includes a control for other device functionality, e.g. illumination.

Exemplary Mechanical Control

In some embodiments, the control is a mechanical control. For example, in some embodiments, a button is coupled to a valve of a material source (e.g. FIG. 20B, valve 2053) and pressing on the button opens the valve, dispensing a quantity of material from the source. In some embodiments, a quantity of material dispensed corresponds to the duration of pressing on the button and/or force at which the button is pressed.

FIG. 25 is a simplified schematic cross sectional view of a device including adjustable volume dispensing, according to some embodiments of the invention. In some embodiments, a material source includes a material storage 2550 coupled to a material dose buffer 2552. In some embodiments, for example, upon a material introduction initiation (e.g. pressing on button 2540), material within dose buffer 2552 is dispensed through nozzle. A potential benefit of dose buffer is uniform dose dispensing, independent of how the user initiates dispensing (e.g. how long/hard the user presses on button 2540).

In some embodiments, a dosage size (quantity of material dispensed) is controlled, for example mechanically, e.g. by moving knob 2554 in or out of device to change a volume (reduce or increase respectively) of dosage storage 2552. In some embodiments, knob screws in and out of device.

In some embodiments, dose buffer 2552 facilitates dispensing at different material pressures. For example, in some embodiments, material from material storage 2550 enters dose buffer 2552, and a pressure of material in dose buffer 2552 is less than pressure of material in material storage. A potential benefit of a dose buffer 2552 is the ability to store material (e.g. in material storage 2550) at pressures higher than a pressure at which introduced material damages the user.

For example, in some embodiments, material is compressed in dose buffer 2552 e.g. before dispensing, potential benefit being, for example, maintaining of dispensed material pressure, e.g. if pressure of material within material storage 2550 decreases as material storage 2550 empties.

Exemplary Control and/or Safety Features

In some embodiments, the control has one or more automatic safety feature. For example, in embodiments where inserted material quantity and/or pressure are user defined, the control prevents insertion of damaging quantities and/or pressures in each treatment.

In some embodiments, a control controls a quantity of material dispensed in a time duration, optionally, over more than one treatment, for example, a control allows only a total amount (optionally over several initiations) which is less than an amount which causes damage to the bladder in a time period. For example, the control allows only up to of 100 cc of material to be introduced in a 3 hour time period. In some embodiments, the time period is a time related to the time taken for material to dissipate out of the bladder.

Exemplary Automated Control

In some embodiments, the control includes a processor with programming, memory and dedicated circuitry. In some embodiments, the processor is programmed to measure and/or store in processor memory dispensed material quantities and/or frequencies. In some embodiments, the processor programming includes a treatment plan, optionally personalized including, for example, dose quantity and/or dispensing pressure.

Exemplary User Interface

In some embodiments, a user initiates dispensing of material from the device and/or controls other device functionality (e.g. illumination, treatment plan) through a user interface e.g. which is coupled through one or more control. In an exemplary embodiment, the user interface is a button 2140.

In some embodiments, the device dispenses an amount of material, e.g. a dose, upon a single press of a button.

In some embodiments, for example, to prevent introducing a traumatic amount of material to the urethra, different types of user initiation (e.g. pressing on a button with different pressure and/or duration) dispense substantially the same amount of material. For example, in some embodiments, independent of how hard or how long button 2140 is pressed (over a threshold) by a user, the device dispenses the same amount of material. Optionally, user increases the amount dispensed by multiple initiations (e.g. pressing repetitively on the button).

Alternatively, in some embodiments, a user controls a quantity of material to be introduced, for example, by pressing harder and/or longer on a button.

In some embodiments, a user interface includes one or more element (e.g. button, switch) for activation/deactivation of an illumination element (e.g. illumination element 2146). Optionally, in some embodiments, a single element controls activation/deactivation of the illumination element and dispensing material.

In an exemplary embodiment, different pressure and/or depth of compression and/or force of compression of button 2140 results in different actions. For example, in some embodiments, a gentle and/or half compression of button 2140 switches on an illumination element and a firm and/or full compression of button 2140 causes dispensing material (e.g. a single dose of material).

In some embodiments, the user interface includes one or more switch. In some embodiments, the user interface includes a screen (e.g. a touch screen). In some embodiments the user interface includes a keypad.

In some embodiments, a user interface displays information to the user, for example, historical dispensing information (e.g. time and/or amount of previous dispensing of material), quantity of material remaining in the material source, battery level etc.

In some embodiments, the device lacks a user interface and/or dispensing is without a user interacting with a user interface element. For example, in some embodiments, once the device is in position at the urethral opening, the device automatically dispenses material (e.g. a single dose of material). For example, in some embodiments, the device being in position is verified using a pressure sensor (e.g. located on or coupled to the device nozzle); for example, once the pressure sensor verifies a seal (e.g. high enough pressure) the device dispenses material (e.g. a dose of material).

Exemplary Shield

In some embodiments, the device includes and/or is coupled to a shield. In some embodiments, the shield protects, for example, a user (e.g. user hands, user clothing) e.g. from urine, discharge, escaped material. In some embodiments, the shield protects the environment e.g. from urine, discharge, escaped material.

In some embodiments, the shield absorbs and/or is impermeable to, for example, urine and/or introduced material. In some embodiments, the shield absorbs and/or is impermeable to, for example, genital discharges e.g. mucus, vaginal discharge, menstrual blood. In some embodiments, a clean and/or new shield is used for each treatment. In some embodiments, a shield is a disposable shield.

Exemplary Personalization

In some embodiments, a device and/or method of treatment is personalized to a particular user.

In some embodiments a shape and/or size of at least a part of a device is personalized. In some embodiments, a shape and/or size of a nozzle is personalized to fit a user. In some embodiments, a relative position of one element to another element (e.g. nozzle and positioning device) is personalized to fit a user.

In some embodiments, a quantity of material and/or a pressure of material introduced is personalized for a user. In some embodiments, a treatment schedule including, for example, duration of each treatment and/or frequency of treatment, is personalized for a user.

Exemplary System for Treating SUI

In some embodiments, a device, for example, as described above, is part of a system for treating stress urinary incontinence.

Optionally, the system includes a processing application, optionally external to the device, for example, for collecting and/or tracking of treatment information e.g. a processing application on a central system, an individual medical center system, as an application on a user's electronic device (e.g. mobile phone, tablet, computer). In some embodiments, connections between elements in the system are wireless.

Optionally, in some embodiments, the system includes diagnostic tools.

Optionally, the system includes a database. In some embodiments, the processing application receives and/or tracks diagnostic measurements, which are optionally used to evaluate treatment and/or design a treatment plan.

In some embodiments, collection of data is automatic, for example, device measurements are automatically recorded in a database. Additionally or alternatively, collection of data is by input into a system user interface, for example a device user interface and/or separate system user interface.

Exemplary Results of Applying Some Exemplary Embodiments of the Invention

An apparatus was constructed to experimentally demonstrate aspects of some embodiments of the invention.

Figure 26:
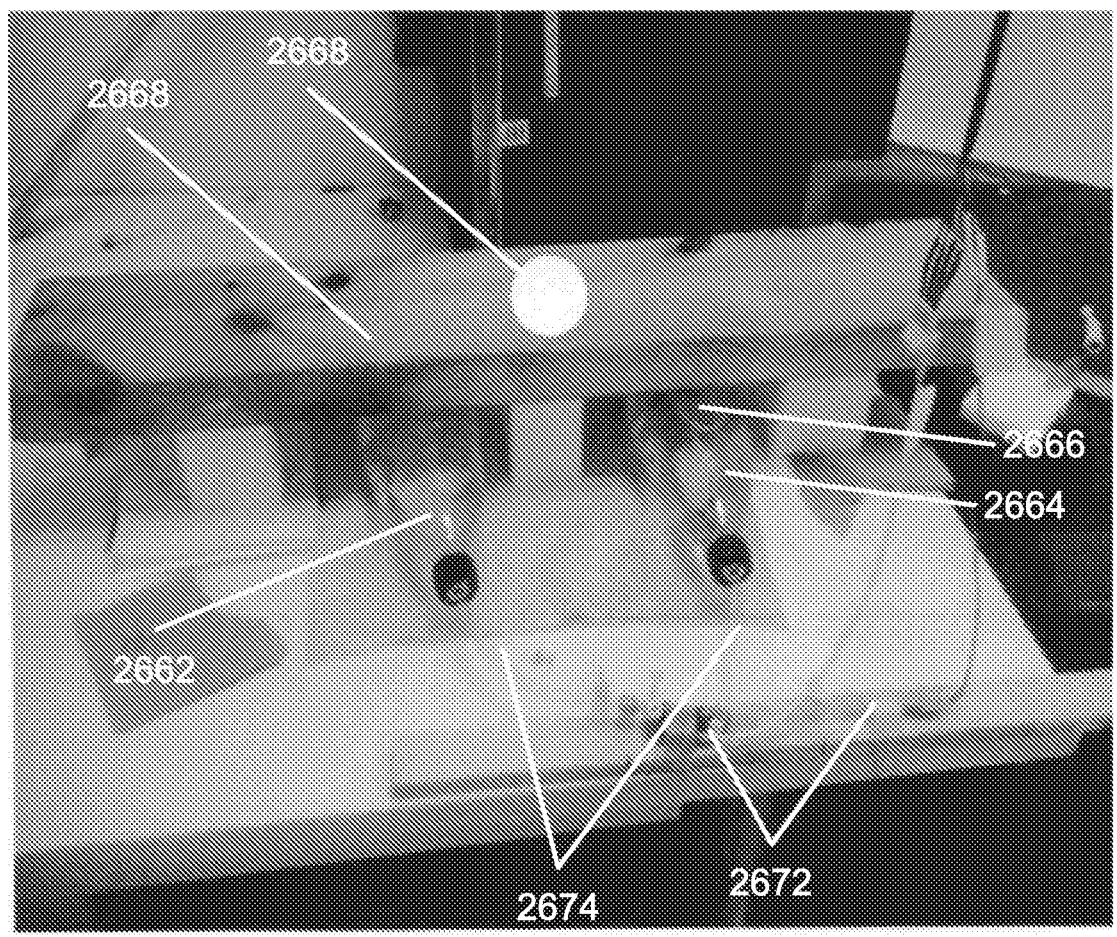
FIG. 26 illustrates an experimental apparatus for comparing an untreated bladder pressure response with a treated bladder pressure response, according to some embodiments of the invention.

FIG. 26 illustrates an experimental apparatus for comparing an untreated bladder pressure response with a treated bladder pressure response, according to some embodiments of the invention. Model bladders were constructed from plastic bottles, were an untreated bladder was modeled by a bottle filled with water 2662 and a treated bladder was modeled by a bottle 2664 partially filled with air 2666. Stress pressure response was modeled by impacting 2668 in the center of a wooden plank 2670 placed over both bottles 2662, 2664. Pressure responses of model bladders was measured using pressure sensors 2672, each pressure sensor fluidly attached by a tube 2674 to a model bladder 2662, 2664.

Figure 27:
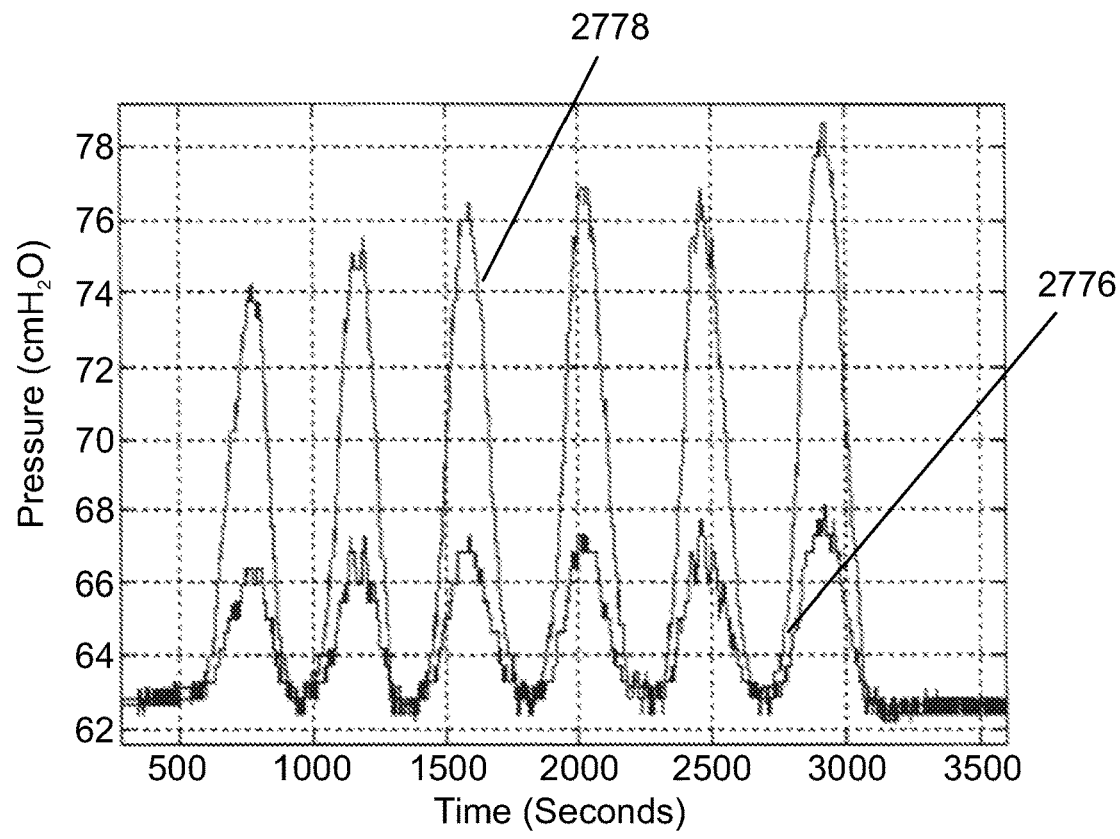
FIG. 27 illustrates a measured modeled stress pressure response of a bladder treated with 25 cc gas and an untreated bladder, according to some embodiments of the invention.
Figure 28:
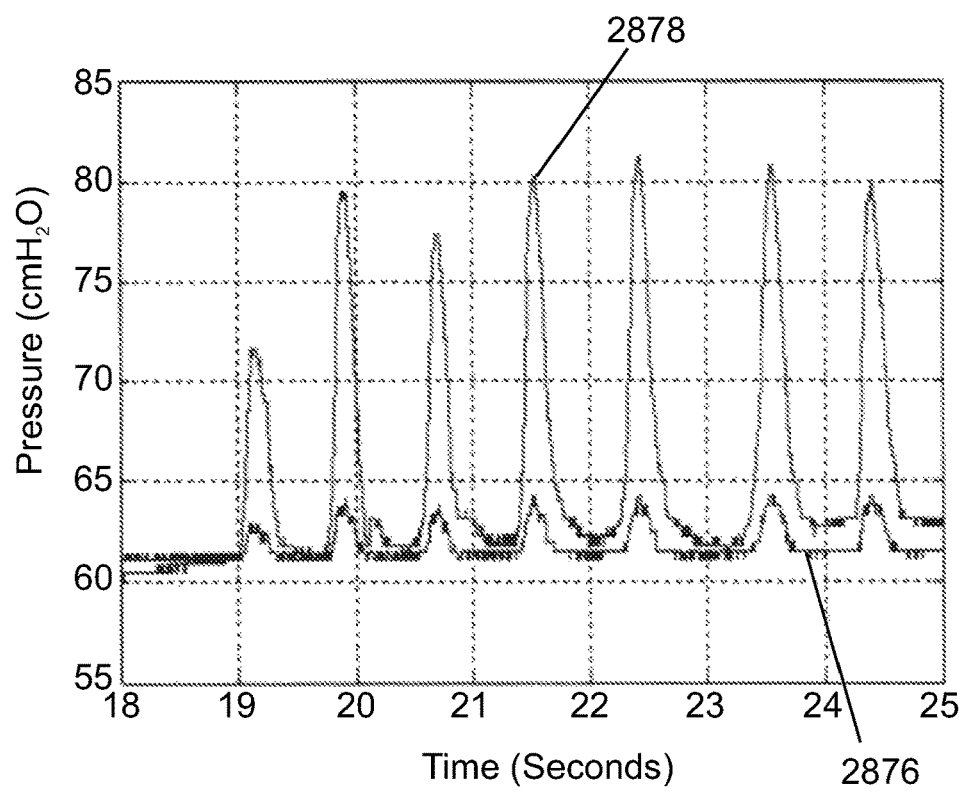
FIG. 28 illustrates a measured modeled stress pressure response of a bladder treated with 50 cc gas and an untreated bladder, according to some embodiments of the invention.

FIG. 27 illustrates a measured modeled stress pressure response of a bladder treated with 25 cc gas 2776 and an untreated bladder 2778, according to some embodiments of the invention. FIG. 28 illustrates a measured modeled stress pressure response of a bladder treated with 50 cc of gas 2876 and an untreated bladder 2878, according to some embodiments of the invention. Each peak on the graphs corresponds to one shock or stress (impact on wooden plank). Both treated bladders exhibit consistent reduced stress pressure peaks compared to the untreated bladder.

An urodynamic diagnostic procedure was performed on subjects suffering from SUI. The procedure included inserting a first pressure sensor into the subject's bladder and a second pressure sensor anally. The pressure sensor in the bladder measured Pves and the anal pressure sensor measured abdominal pressure, Pabd. Detrusor muscle induced pressure, Pdet, was calculated as the difference between measured abdominal and bladder pressure; Pdet=Pves−Pabd. Detrusor muscle induced pressure is, in some embodiments, used as a measure of pressure on the urethral sphincter and, in some embodiments, is used as an indication of the likelihood of leakage from the bladder.

Figure 29:
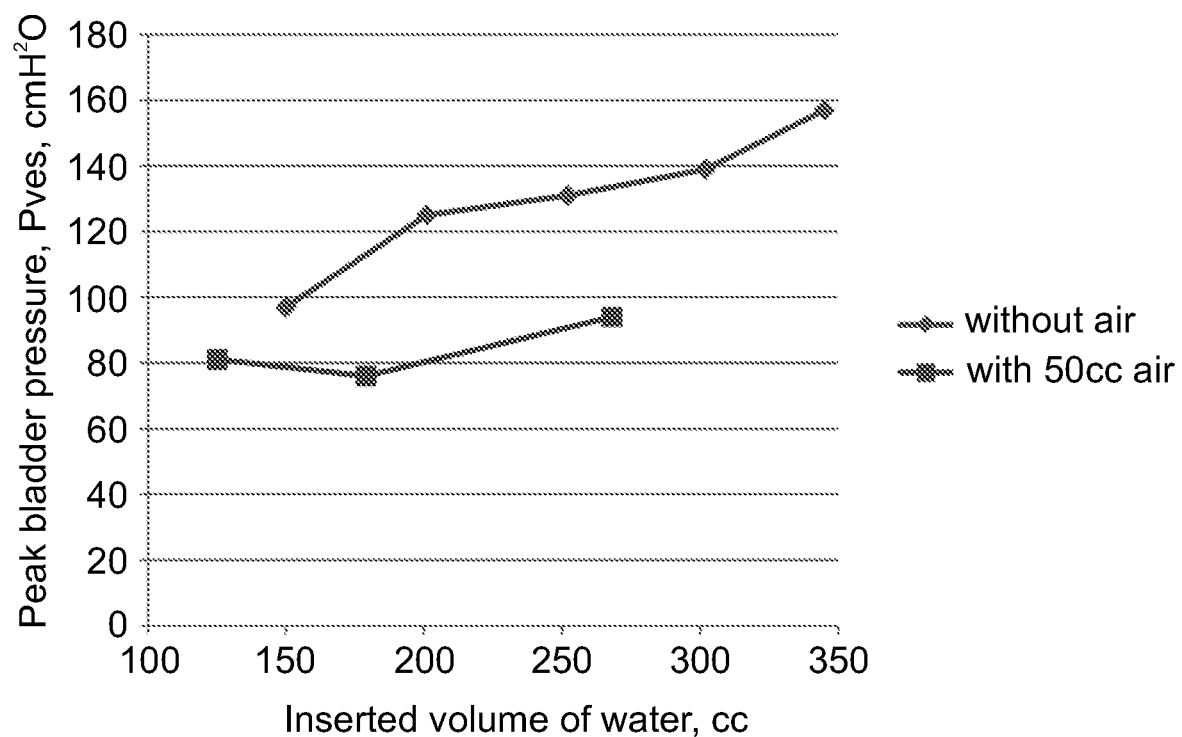
FIG. 29 illustrates bladder pressure measurements for a patient, according to some embodiments of the invention.

FIG. 29 illustrates bladder pressure measurements for a patient collected during an urodynamic diagnostic procedure, according to some embodiments of the invention. The urodynamic diagnostic procedure included emptying the patient's bladder and then refilling the bladder where the insertion of liquid (saline) was measured, providing an indication of bladder volume. At different levels of fluid insertion, the patient coughed, providing a bladder pressure peak. The bladder was then emptied, and 125 ml of saline was inserted, along with 50 cc of air, which was inserted into the subject's bladder using a standard 50 cc syringe. Peak bladder pressure was then measured (the peak pressure provided by the patient coughing), and re-measured for additional insertions of liquid (saline). Results of the procedure are shown on FIG. 29. The results illustrate reduced peak pressure for a bladder treated according to embodiments of the invention.

Urodynamic diagnostic procedures, as described above, were performed on five patients. The results illustrate peak detrusor pressure reduction for bladders treated according to embodiments of the invention. Results are illustrated in Table 1, below. During testing some patients experienced urine leakage and some patients did not. However, in some embodiments, severity of the SUI condition is assessed by Pdet independent of the presence of leakage (or lack thereof).

TABLE 1

| Patient | Pdet (cm $H_2O$) during peak stress, untreated bladder | Pdet (cm $H_2O$) during peak stress, bladder treated with 50 cc air |
| --- | --- | --- |
| 1 | 18 | 5 |
| 2 | 26 | 7 |
| 3 | 24 | 23 |
| 4 | 37 | 20 |
| 5 | 14 | 11 |

In some embodiments, a method of identifying patients for which treatment according to aspects of the invention is effective includes; treating the patient (e.g. by insertion of air into the patient's bladder) and measuring reduction in peak bladder pressure after treatment and/or identifying and/or measuring reduction in urine leakage.

In some embodiments, pressure reduction of over a threshold value and/or threshold percentage indicates suitability of treatment and/or efficacy of treatment according to embodiment/s of the invention. For example, in some embodiments, treatment is considered effective for patients and/or patients are suitable candidates for treatment using embodiments of the invention, with a measured reduction in peak pressure of more than 1 cm $H_2O$, or more than 5 cm $H_2O$, or more than 10 cm $H_2O$ or lower or higher or intermediate reductions in pressure. For example, in some embodiments, treatment is considered effective and/or patients are suitable candidates for treatment using embodiments of the invention, for patients with a measured reduction in peak pressure, after treatment, of more than 10% or more than 20% or more than 40% or lower, or higher or intermediate percentages.

In some embodiments, patients with low peak pdet before treatment (e.g. less than 10 cm $H_2O$, or less than 15 cm $H_2O$, or less than 5 $H_2O$) are is considered suitable for treatment according to embodiments of the invention. In some embodiments, patients with high peak pdet before treatment (e.g. more than 10 cm $H_2O$, or more than 15 cm $H_2O$, or more than 5 $H_2O$) are considered suitable to treatment according to embodiments of the invention.

Referring to Table 1, in some embodiments, results show that, all patients, after treatment (50 cc of air), had a reduction in peak pressure. Furthermore, for patients 50 cc of air, was highly effective at reducing peak pressure: Patients 1, 2 and 4 who had reduction in pressure of more than 10 cm $H_2O$.

Additionally or alternatively, in some embodiments, reduction in urine leakage, e.g. where reduction is over a threshold where the threshold is an amount of urine and/or a leak-free time indicates suitability and/or efficacy of treatment. In some embodiments, urine leakage is measured and/or reported by a patient after treatment e.g. after self-treatment. In some embodiments, efficacy and/or suitability of a patient for treatment according to embodiments of the invention is assessed without performing an urodynamic diagnostic procedure.

In some embodiments, a patient undergoes an urodynamic diagnostic procedure, where collected measurements are used to identify suitable treatment, e.g. amount and/or pressure and/or frequency of dispensation of material from a device according to some embodiments of the invention. In some embodiments, measurements from an urodynamic diagnostic procedure are used to design a personalized treatment plan e.g. personalization as described above, e.g. a personalized amount and/or pressure and/or frequency of introduction of material into the bladder e.g. reduction and/or continuation of medication to treat the incontinence. In some embodiments, measurements from an urodynamic diagnostic procedure are used to establish safety limits for a treatment plan, e.g. maximum amount and/or pressure of inserted material and/or frequency of treatment.

In some embodiments, additionally or alternatively, pressure measurements are used to identify suitable treatment, for example, treatment using medication, e.g. systemic medication and/or medication inserted into the bladder according to embodiments of the invention.

In some embodiments, a urodynamic diagnostic procedure is performed on a patient who has self treated, for example, according to embodiments of the invention, e.g. using a device (e.g. as described above). In some embodiments, measurements are used to assess suitability of the patient for treatment and/or to assist the patient in effective self-treatment.

General

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for self-treatment of incontinence comprising:
a handheld device body;
a nozzle with a rounded nozzle tip extending from the device body, and sized for at least partial insertion into a urethra;
a source of compressed material located within the device body, and coupled to said nozzle where a pressure of said compressed material is less than 200 cm H2O; and
a control located within the device body, for control of flow of said material from said source into the urethra through said nozzle;
wherein said pressure of said compressed material opens said urethra from the nozzle tip to a bladder;
wherein said compressed material is configured to flow into said bladder through the urethra to provide a cushion material within said bladder for resisting urine leakage; and
wherein the device body further comprises an inlet for collection of compressible material, and the source of compressed material comprises a pump coupled to said inlet, for compression of collected compressible material.

2. The device of claim 1, wherein at least a portion of said nozzle is sized and shaped to seal against the urethra.

3. The device of claim 1, wherein said nozzle is sufficiently rigid such that the nozzle can be inserted into the urethra when the device is directed using said device body.

4. The device of claim 1, wherein said nozzle comprises a portion normally inverted inside a body of said nozzle; wherein said pressure of said compressed material uninverts said portion.

5. The device of claim 1, wherein said source further comprises:
a material container for storing the compressed material therein;
wherein the pump compresses the collected compressible material into said material container.

6. The device of claim 1, wherein said control prevents more than a maximum quantity of said compressed material from being dispensed within a time period.

7. The device of claim 1, comprising a positioning element for aligning said nozzle to the urethra.

8. The device of claim 7, wherein at least a portion of said positioning element is sized and shaped for placement in a body portion.

9. The device of claim 7, wherein said positioning element comprises a visual element to provide a user with at least one visual clue as to a location of at least a portion of the device with respect to the urethra.

10. The device according to claim 9, wherein said positioning element comprises a mirror.

11. The device of claim 9, wherein said positioning element comprises a camera.

12. The device of claim 1, wherein said compressed material is a gas.

13. The device of claim 1, wherein said compressed material is atmospheric air.

14. The device of claim 1, wherein said compressed material is a mixture of liquid and compressible elements.

15. The device according to claim 14, wherein said compressible elements are gas bubbles.

16. The device of claim 1, wherein said compressed material comprises medication.

17. The device according to claim 16, wherein said medication is selected from the group consisting of chemotherapy medication, antibiotics, bladder over activity medication and combinations thereof.

18. The device according to claim 1, wherein said pressure of said compressed material is more than 70 cm H2O.

19. The device according to claim 1, wherein a maximum extent of the device is less than 30 cm.

20. A device for self-treatment of incontinence comprising:
a handheld device body;
a source of compressed material located within the device body where a pressure of said compressed material is less than 200 cm H2O;

a rounded nozzle, coupled to said source and extending from the device body, adapted to form a seal against genital tissue around a urethra, said seal able to withstand said pressure of said compressed material;

a control located within the device body, for control of flow of said compressed material from said source into the urethra through said nozzle;

wherein said pressure is sufficient to open the urethra from a urethral opening to a bladder, wherein, said compressed material is configured to flow into the bladder through the urethra to provide a cushion material within the bladder for resisting urine leakage; and wherein the device body further comprises an inlet for collection of compressible material, and the source of compressed material comprises a pump coupled to said inlet, for compression of collected compressible material.

21. The device of claim 20, wherein said source further comprises:

a material container for storing the compressed material therein;

wherein the pump compresses the collected compressible material into said material container.

22. The device of claim 20, wherein said control prevents more than a maximum quantity of said compressed material from being dispensed within a time period.

23. The device of claim 20, wherein said compressed material is a gas.

24. The device of claim 20, wherein said compressed material is atmospheric air.

25. The device of claim 20, wherein said compressed material is a mixture of liquid and compressible elements.

26. The device according to claim 25, wherein said compressible elements are gas bubbles.

27. The device of claim 20, wherein said compressed material comprises medication.

28. The device according to claim 27, wherein said medication is selected from the group consisting of chemotherapy medication, antibiotics, bladder over activity medication and combinations thereof.

29. The device according to claim 20, wherein the pressure of said compressed material is more than 70 cm H2O.

30. The device according to claim 20, wherein a maximum extent of the device is less than 30 cm.

31. A non-traumatic method of self-treatment of stress urinary incontinence comprising:

introducing into a urethra a quantity of a compressed material using a device comprising a handheld device body, a nozzle with a rounded nozzle tip extending from the device body, and sized for at least partial insertion into the urethra, a source of the compressed material located within the device body and coupled to said nozzle, a control located within the device body for control of flow of said material from said source into the urethra through said nozzle, the device body further comprising an inlet for collection of compressible material, the source of compressed material comprising a pump coupled to said inlet for compression of the collected material, wherein the compressed material exits from the nozzle into the urethra, the quantity of said compressed material is less than 200 cc, a pressure of said compressed material is less than 200 cm H2O and said pressure is sufficient to open at least a portion of said urethra proximal to a bladder, whereby said compressed material is configured to flow into said bladder through the urethra to provide a cushion material within the bladder for resisting urine leakage;

wherein said introducing is by a user of the device; and wherein said urethra is the urethra of the user.

32. The method of claim 31, wherein said introducing is repeated.

33. The method according to claim 32, wherein less than a maximum quantity of said compressed material is dispensed in a time period.

34. The method of claim 31, wherein said introducing is upon a user input.

35. The method of claim 31, wherein said quantity of said compressed material is defined by a user input.

36. The method according to claim 31, further comprising a step of providing said compressed material by compressing an air.

37. The method of claim 31, wherein said compressed material in said bladder reduces a peak bladder shock pressure response to below a pressure at which the urethra opens ($p_{ura}$).

38. The method of claim 31, further comprising a step of aligning the nozzle to said urethra.

39. The method according to claim 31, wherein the pressure of said compressed material is more than 70 cm H2O.

* * * * *